United States Patent [19]

Poggie et al.

[11] Patent Number: 5,250,050
[45] Date of Patent: Oct. 5, 1993

[54] APPARATUS FOR KNEE PROSTHESIS

[75] Inventors: Matthew P. Poggie, Union City, N.J.; Peter S. Walker, Northwood, England; Frederick C. Ewald, Weston, Mass.

[73] Assignee: Pfizer Hospital Products Group, Inc., New York, N.Y.

[21] Appl. No.: 876,642

[22] Filed: Apr. 30, 1992

Related U.S. Application Data

[62] Division of Ser. No. 645,388, Jan. 24, 1991, Pat. No. 5,116,338, which is a division of Ser. No. 151,734, Feb. 3, 1988, Pat. No. 5,002,547.

[30] Foreign Application Priority Data

Feb. 7, 1987 [GB] United Kingdom ................. 8702789

[51] Int. Cl.⁵ ............................................. A61B 17/00
[52] U.S. Cl. ........................................ 606/79; 606/82; 606/88; 606/89
[58] Field of Search ................. 606/62, 75, 79, 82, 606/86-90, 96, 177, 178

[56] References Cited

U.S. PATENT DOCUMENTS

| | | | |
|---|---|---|---|
| 4,524,766 | 6/1985 | Petersen | 606/88 |
| 4,718,413 | 1/1988 | Johnson | 606/96 X |
| 4,841,975 | 6/1989 | Woolson | 606/96 X |

Primary Examiner—Robert A. Hafer
Assistant Examiner—Brian E. Hanlon
Attorney, Agent, or Firm—Peter C. Richardson; Lawrence C. Akers; Raymond W. Augustin

[57] ABSTRACT

A modulator apparatus for use in the preparation of bone surfaces and the implantation of a modular total knee prosthesis in a patient, which apparatus comprises cutting guides, templates, alignment devices, a distractor and clamping instruments which provide modularity and facilitate bone resection and prosthesis implantation.

1 Claim, 21 Drawing Sheets

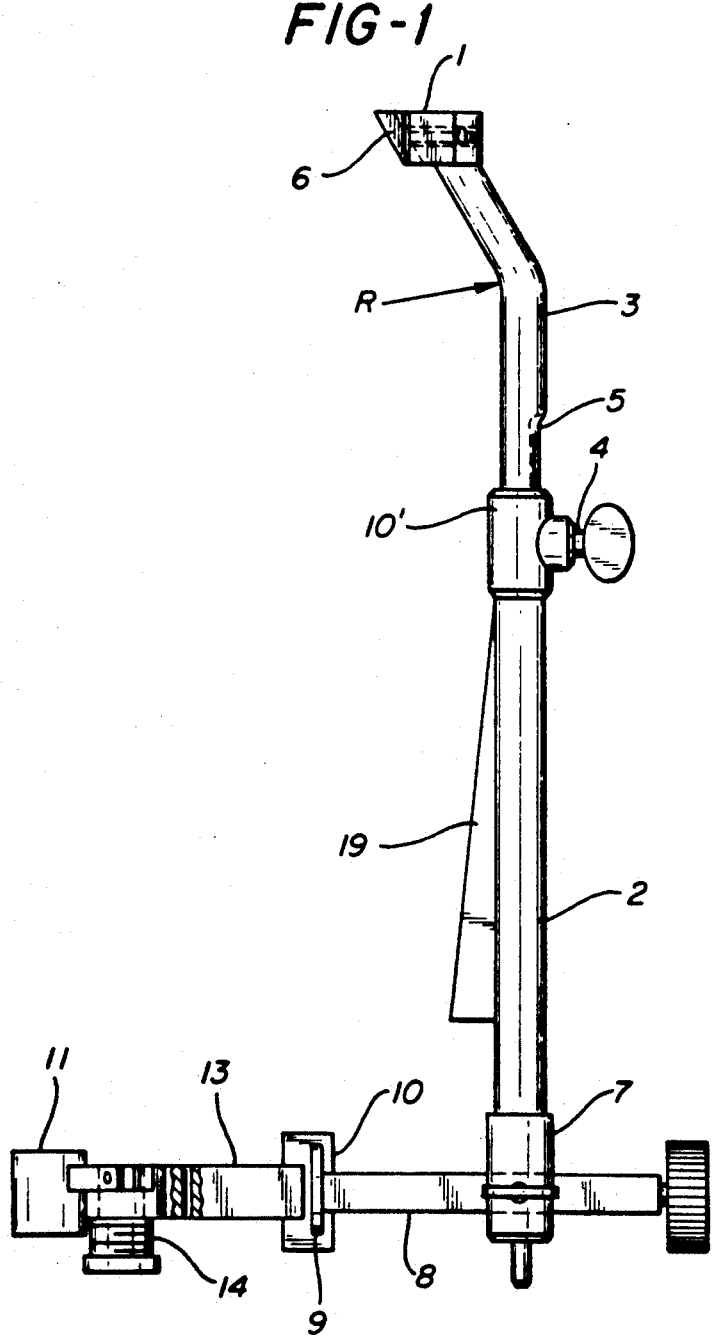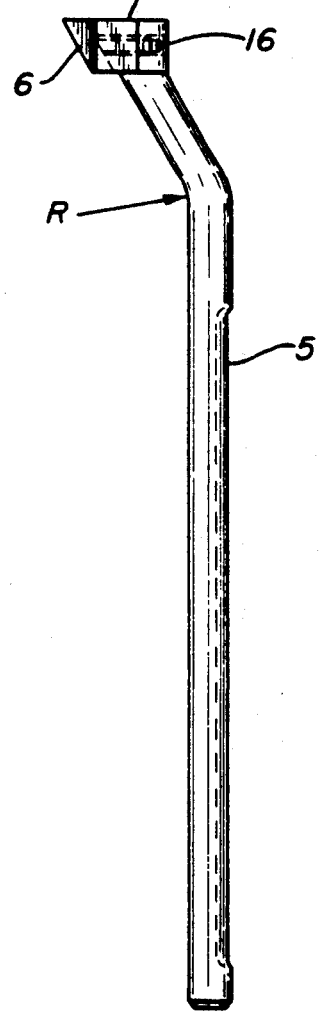

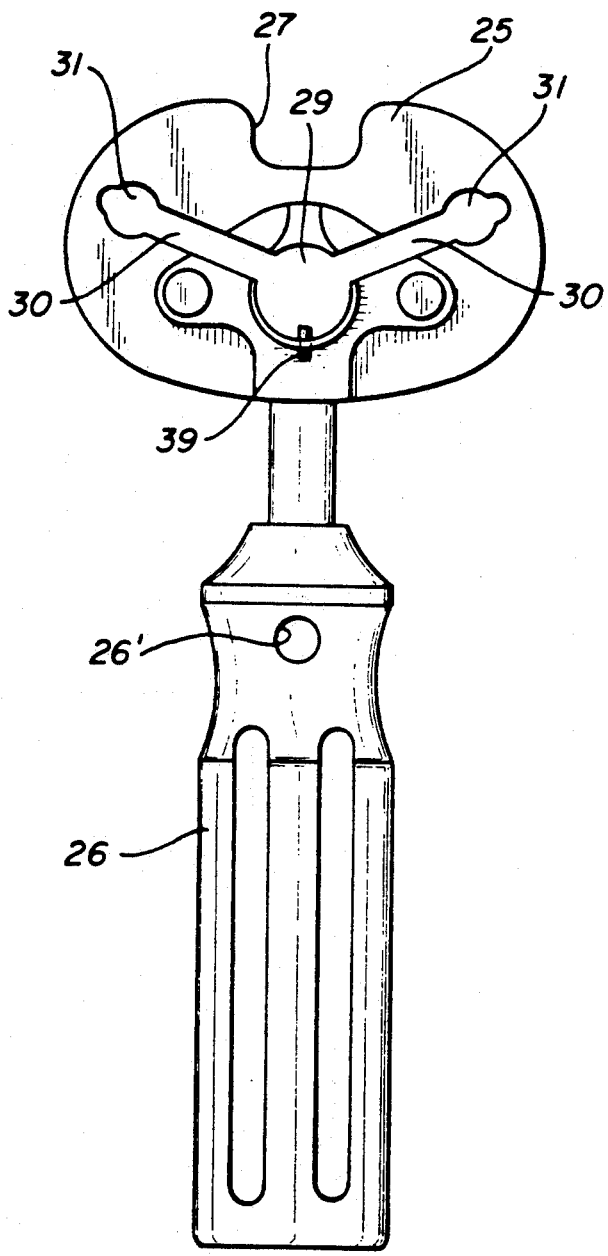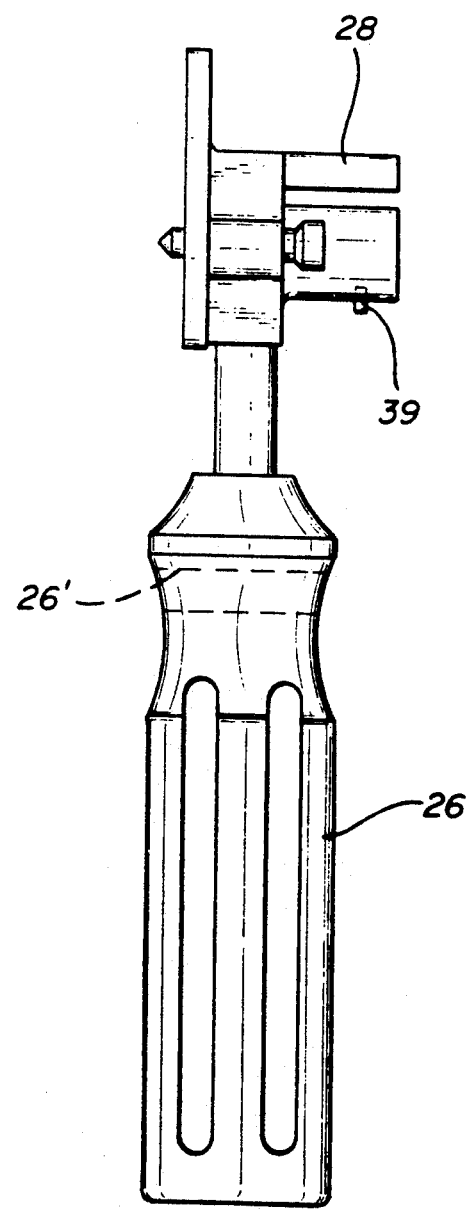

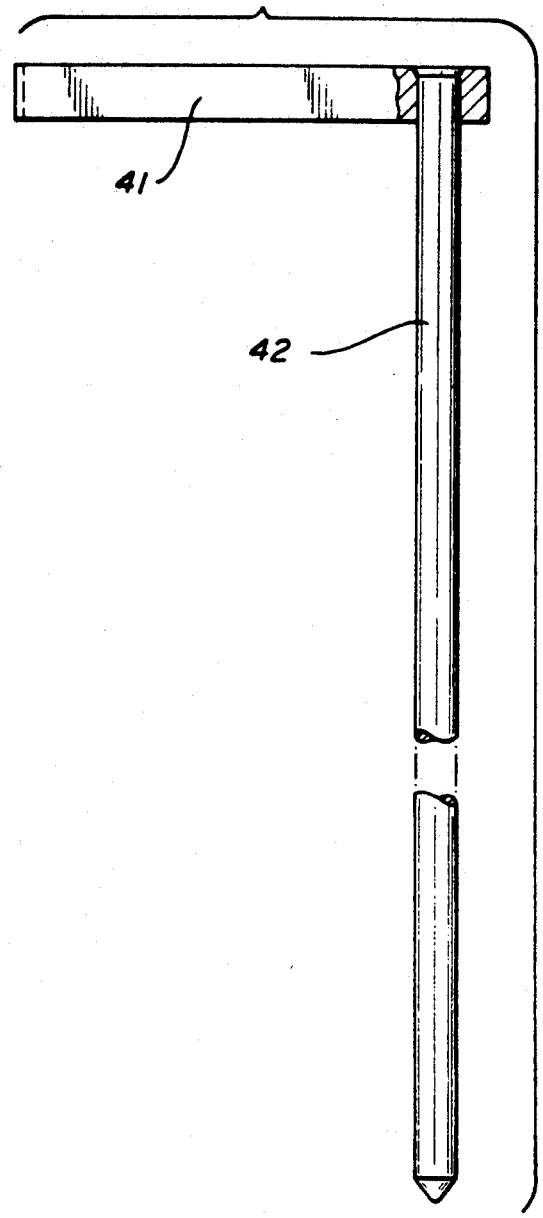
FIG-12
FIG-13
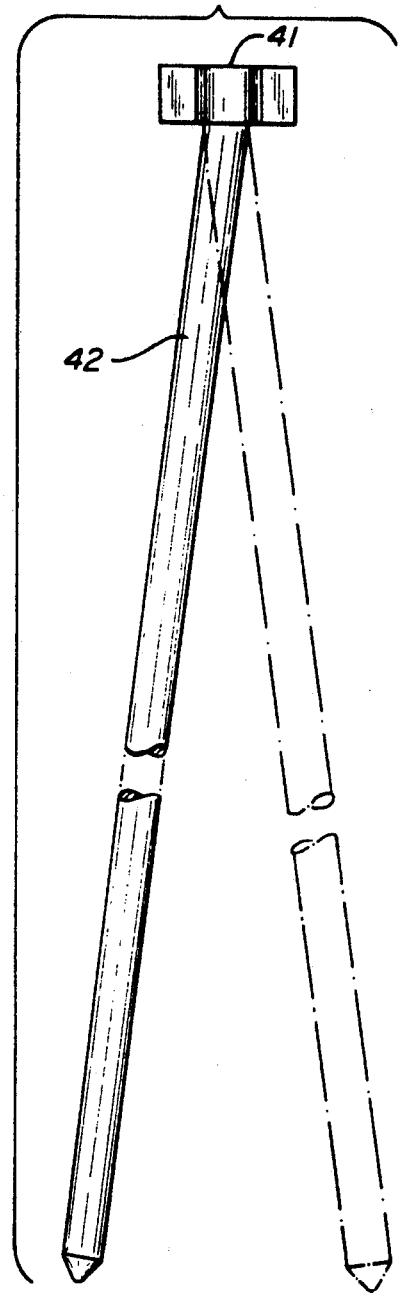
FIG-14

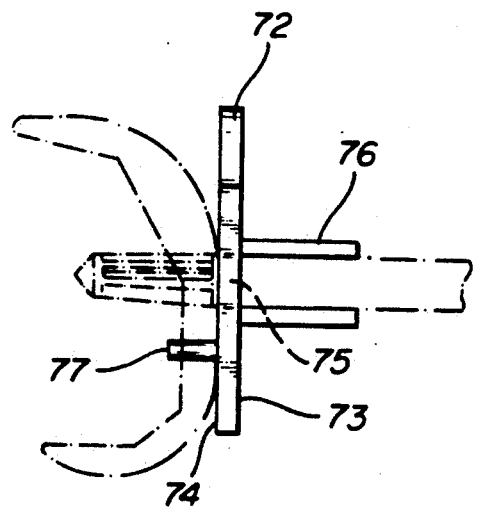
FIG-27
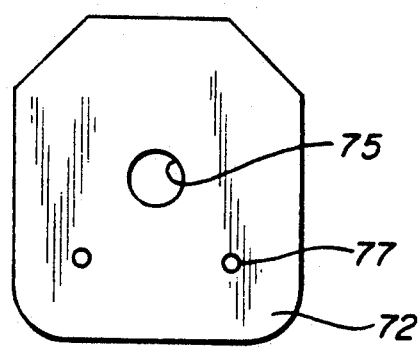
FIG-28
FIG-29
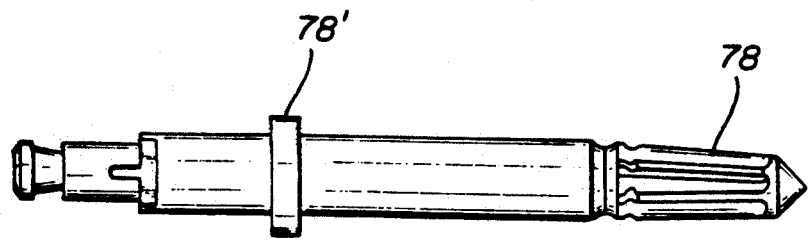

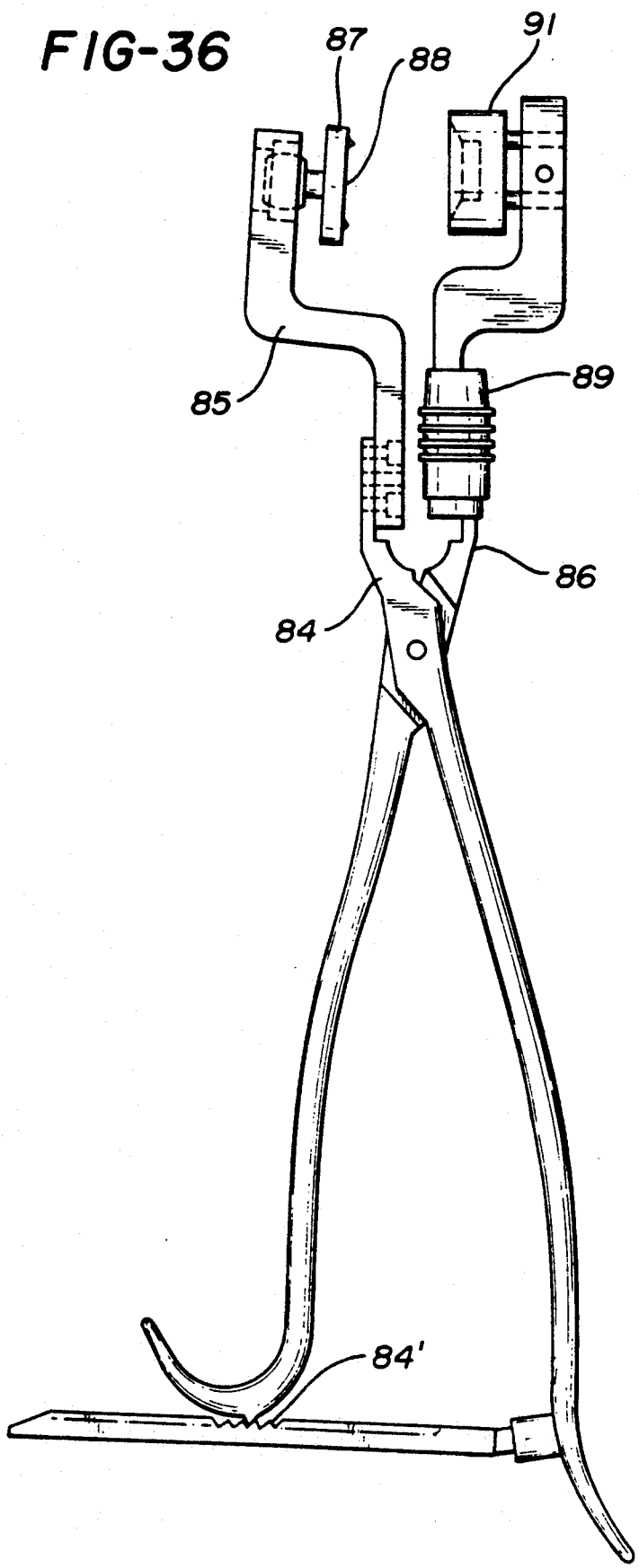
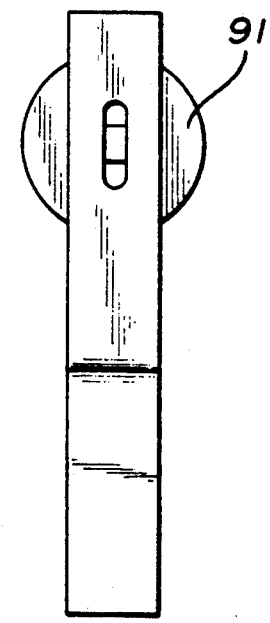

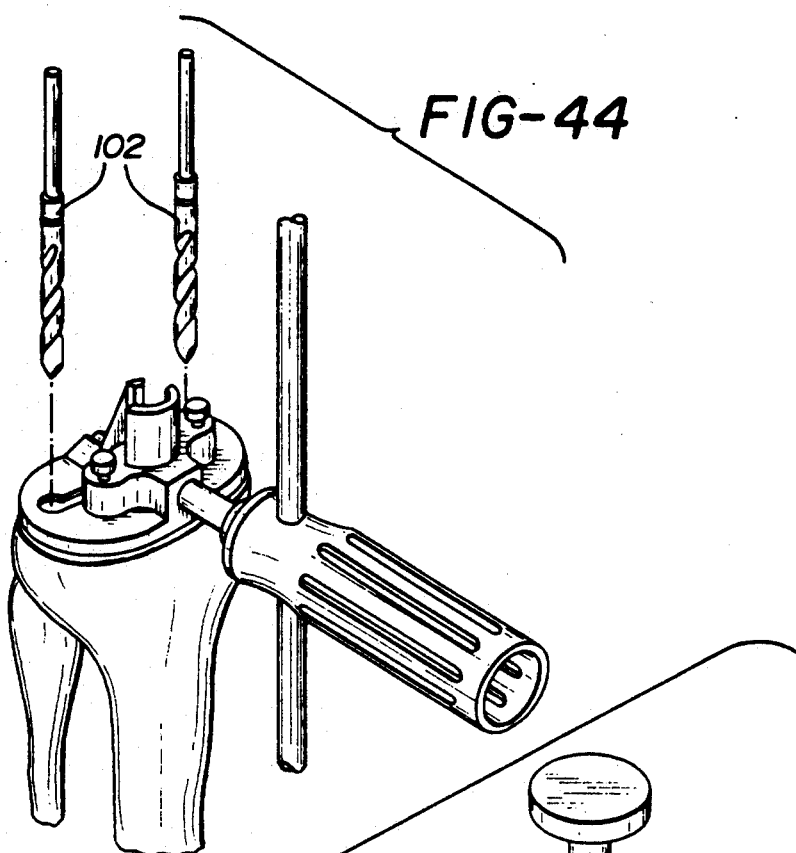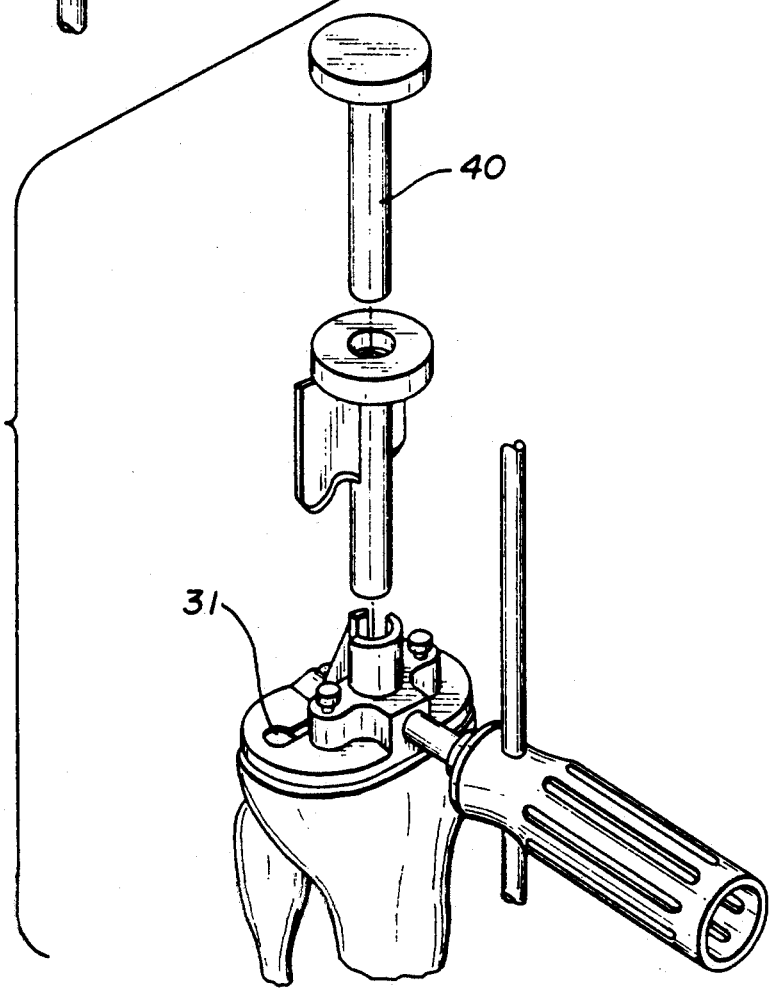

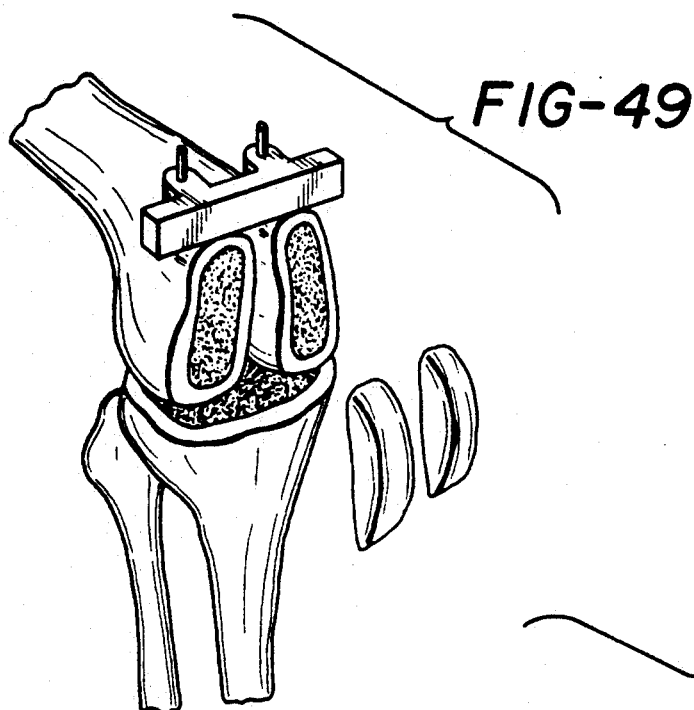
FIG-49
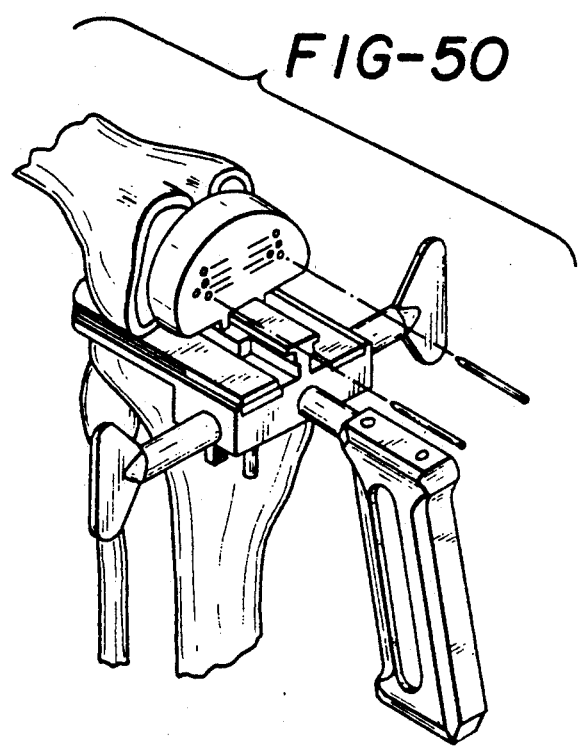
FIG-50
FIG-51
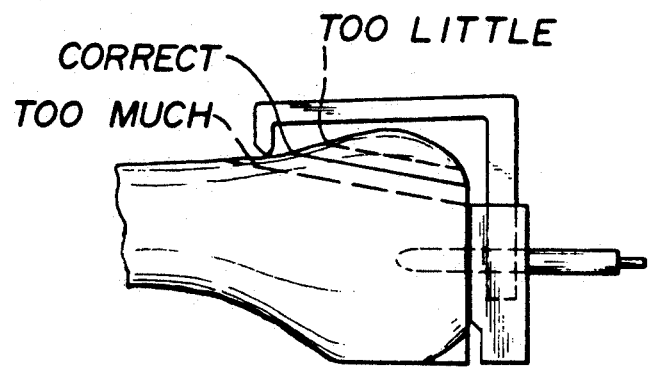

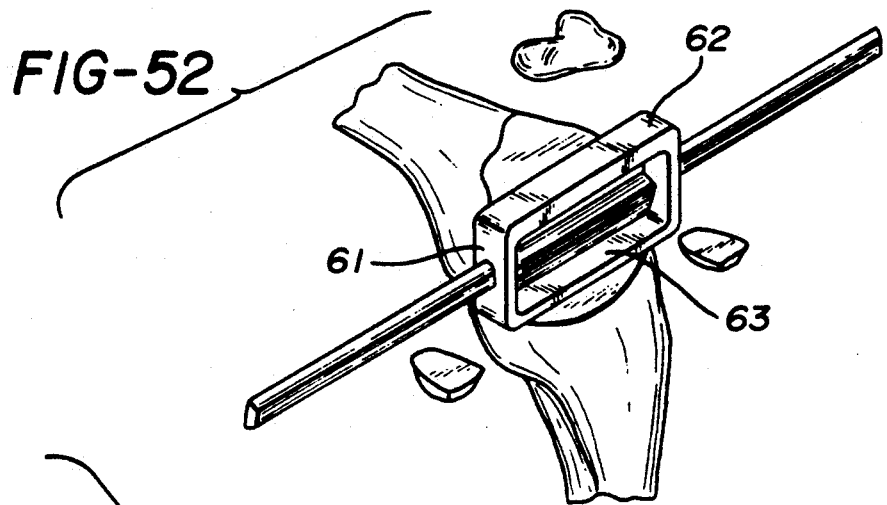
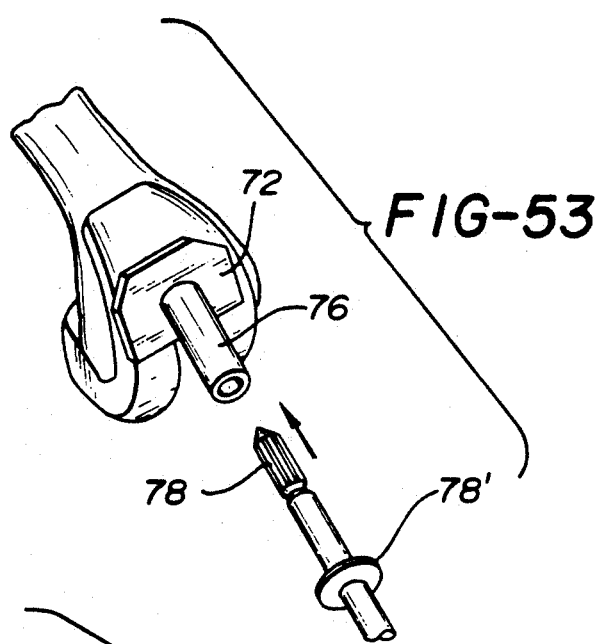
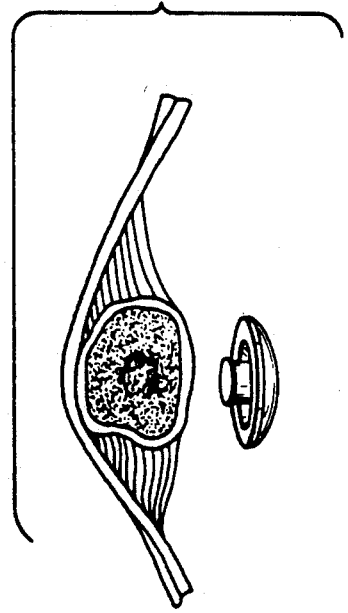
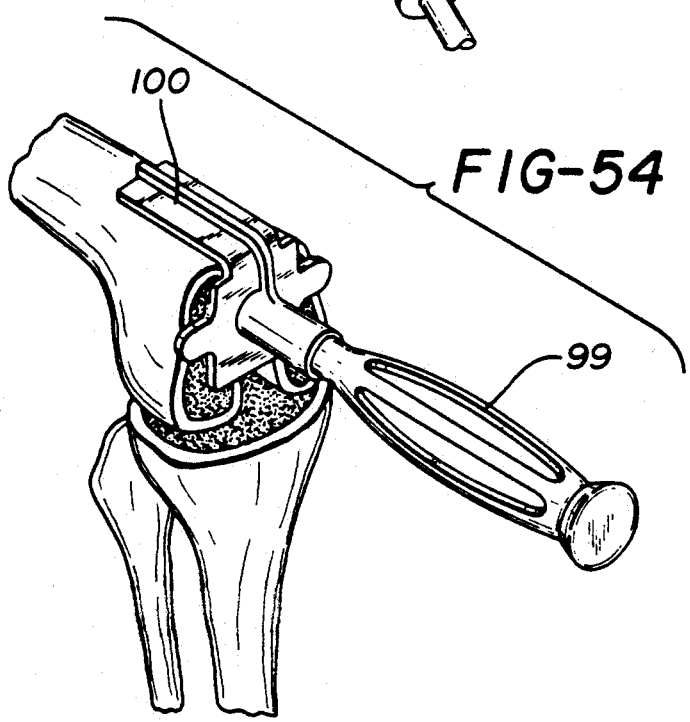

5,250,050

APPARATUS FOR KNEE PROSTHESIS

This is a division of application Ser. No. 645,388, filed on Jan. 24, 1991, now U.S. Pat. No. 5,116,338, which was a divisional of application Ser. No. 151,734, filed Feb. 3, 1988, now U.S. Pat. No. 5,002,547.

FIELD OF INVENTION

The present invention relates to apparatus for a knee prosthesis. More particularly the invention is concerned with a modular apparatus for use in the preparation of bone surfaces and the implantation of a modular total knee prosthesis.

BACKGROUND OF THE INVENTION

The human knee joint is subject to greater stress than any joint in the body. This is because it must bear the full weight of the body, often at disadvantageous leverage ratios. Consequently, there is a premium on the design of a prosthesis for replacement of the knee joint.

Additionally, the implantation of a prosthesis should avoid resection of any more of the joint than is strictly necessary. This is especially true of the knee which includes ligaments within the joint, i.e., the cruciate ligaments which are important for the future functioning of the joint, and, therefore, in the design of the prosthesis it is important to keep the thickness of the prosthesis to a minimum so as to avoid resection, but yet to do so without sacrificing consistent and long term adequate performance.

Other factors to be considered in the design of a knee prosthesis include the need to anchor it against the forces of shear, tipping, and torque to which the knee joint is particularly susceptible.

Furthermore, it is desirable to standardize the manner in which the prosthesis is implanted and to provide instrumentation by which the tibial plateau and femur are resected in such a way as to make the excisions fit with the components to be applied to the plateau.

An improved modular total knee prosthesis which meets the challenge of restoring a natural, individual knee motion pattern and derived from substantial clinical experience, detailed anthopometric data and state-of-the-art computer graphic stimulations is described and claimed in copending applications Ser. No. 52033 and Ser. No. 97286.

Application Ser. No. 52033 provides a tibial component and application Ser. No. 97286 provides, in combination, a femoral component and tibial plateau. The disclosures in both these applications are incorporated herein by reference.

The present invention is concerned with improved instrumentation to facilitate implantation of a total knee prosthesis such as disclosed in (but not limited to) the aforementioned applications.

SUMMARY OF THE INVENTION

In accordance with the present invention there is provided a modular apparatus for use in the preparation of bone surfaces and the implantation of a modular total knee prosthesis in a patient, which apparatus comprises:

(a) an extendable rod having a distal end and a proximal end, means for adjusting the length of the rod, means for adjusting the lateral alignment and angular orientation of the proximal end of the rod, clamp means associated with the distal end of said rod for clamping said distal end to the ankle region of the patient's leg and combination fixing means and cutting platform associated with said proximal end of the rod for attaching said proximal end to the upper end of the patient's tibia while aligning the cutting platform close to the tibial plateau;

(b) an adjustable stylus for aligning said cutting platform at the correct level for resecting the tibial plateau;

(c) a modular stem/fin template for determining the peripheral size of the resected proximal tibia and including a raised cylindrical hollow tube for aligning a stem/fin punch;

(d) a stem/fin punch comprising a central hollow cylindrical tube with a distal chisel edge and two fins extending radially from said tube at a predetermined angle and each having a distal chisel edge;

(e) a push rod which fits into said hollow cylindrical tube of said stem/fin punch;

(f) an alignment fork attached to an intramedullary rod adapted to be introduced into a medullary canal of the patient;

(g) a femoral distractor comprising a handle, a rail adapted to slide onto the alignment fork, a lateral arm and a medial arm, each of which has associated means for separately raising and lowering each arm;

(h) a drill guide adapted to slide along the rail of the femoral distractor and having a plurality of holes for accepting locating pins;

(i) a distal cutting guide comprising a flat plate having a top surface and a bottom surface and integral flanges extending from said bottom surface and each being inset from one edge of said surface, each of said flanges having a locating hole extending therethrough;

(j) a modular cutting guide for guiding a saw blade to make cuts required for a femoral component prosthesis, comprising a substantially rectangular block having a flat top surface and a flat bottom surface and, located between said top surface and said bottom surface, an intermediate solid block having an angled top surface and an angled bottom surface, each of said angled surfaces providing a guide for making a chamfer cut;

(k) a femoral sizer for determining the size of the patient's femur, comprising a body portion having locating holes, a central tubular orifice for accepting a feeler element and indicating means for indicating the depth of the feeler element within said orifice when the sizer is located on the patient's femur, thereby providing a determination of the sizer required for a modular cutting guide;

(l) a reamer guide for correct location of a reamer for preparing a cavity to locate a femoral prosthesis peg, which reamer guide comprises a flat plate having a top surface and a bottom surface, a hole extending through the plate, a tubular bushing extending from said top surface and lined up with said hole and locating pegs extending from said bottom surface;

(m) a patella resection guide comprising a scissor-type clamp having distal gripping arms, each of said arms defining a cutting surface and gripping teeth, said gripping teeth being inset below the plane of the associated cutting surface;

(n) a patella handling instrument providing alternative template and clamping functions comprising a scissor-type member having a first pivotal arm with a distal end and a second pivotal arm with a distal end; the first arm having a swivable platform located at its distal end, the surface of said platform facing inwardly toward said second arm and said second arm having means to interchangeably grip and hold either: (i) a modular patella template having holes to accept drills, or (ii) a clamp member adapted to clamp a patella prosthesis to a resected patella.

DETAILED DESCRIPTION OF THE INVENTION

The total apparatus defined above is a novel and unique combination of numerous elements some of which are novel per se and some of which are modified and improved versions of instruments which performed similar functions in the prior art. However, the overall effect of the present novel combination apparatus is to facilitate bone preparation and prosthesis implantation and also provide a degree of modularity hitherto unknown.

The apparatus is particularly adapted for use with the improved prosthesis disclosed in the copending applications acknowledged hereinabove and the invention will be more particularly described with reference to the implantation of preferred embodiments of such prosthesis.

DESCRIPTION OF THE DRAWINGS

Preferred embodiments of the various elements of the present apparatus are illustrated in the accompanying drawings in which:

FIG. 1 is a side elevation of a combination extendable rod, integral cutting platform and ankle clamp according to the invention;

FIG. 2 is a side elevation of the solid extendable rod and cutting platform of FIG. 1;

FIG. 6 is a top plan view of a modular stem/fin template;

FIG. 7 is a side elevation of the template of FIG. 6;

FIG. 12 is a side elevation of an intramedullary rod and alignment fork;

FIG. 13 is an end elevation of the rod of FIG. 12, showing the alignment fork.

FIG. 14 is another side elevation of the rod of FIG. 12 showing the angulation of the rod relative to the fork;

FIG. 27 is a side elevation of a reamer guide positioned against a femoral template.

FIG. 28 is an end elevation of the reamer guide of FIG. 27;

FIG. 29 is a side elevation of a reamer for reaming the cavity to accommodate a femoral peg;

FIG. 36 is a side elevation of an instrument of FIG. 32 but with a clamp member in place of the patella template;

FIG. 37 is a plan view of the clamp element of FIG. 36;

FIGS. 41 to 55 are schematic representations illustrating the manner in which the instrumentation illustrated in the above-described drawings is utilized to prepare bone surfaces and the procedures illustrated in these schematic drawings will be described in more detail hereinafter.

Referring to the embodiments illustrated in the drawings, FIG. 1 illustrates an instrument for the correct alignment of a cutting surface to facilitate the resection of a tibial plateau 43 (see FIG. 43) to receive a tibial implant, which instrument comprises an extendable rod 10 having a hollow distal portion 2 and a solid proximal portion 3, said distal portion comprising a hollow cylindrical tube 2 and said proximal portion comprising a solid cylindrical rod 3 which slidably fits within said hollow cylindrical tube and means for locking the slidable rod within said tube when the desired overall length is achieved. In the preferred embodiment said means for locking the slidable solid rod 3 within the hollow cylindrical tube 2 comprises a locking screw 4 which tightens within a groove 5 extending longitudinally along said solid rod, the locking preventing both rotational and longitudinal movement. The proximal end of the solid rod has a predetermined radius of curvature R and terminates in an integral cutting platform 6 defining a flat cutting surface 1. The distal end of said hollow cylindrical tube terminates in a bearing 7 which slides radially along a rail 8 extending substantially perpendicularly from a flat plate 9 located in a groove 10 within which said plate may slide laterally, said groove being integral with a pair of tension spring clamping jaws 11, said radial and lateral sliding movement providing means for correctly aligning said cutting platform close to the tibial plateau.

Each of the jaws 11 open and close about a pivot 12 at the end of an arm 13 and is held in a gripping position by a tension spring 14.

Figure 3:
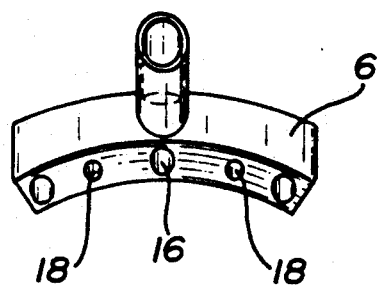
FIG. 3 is a bottom plan view of the cutting platform of FIG. 1.
Figure 4:
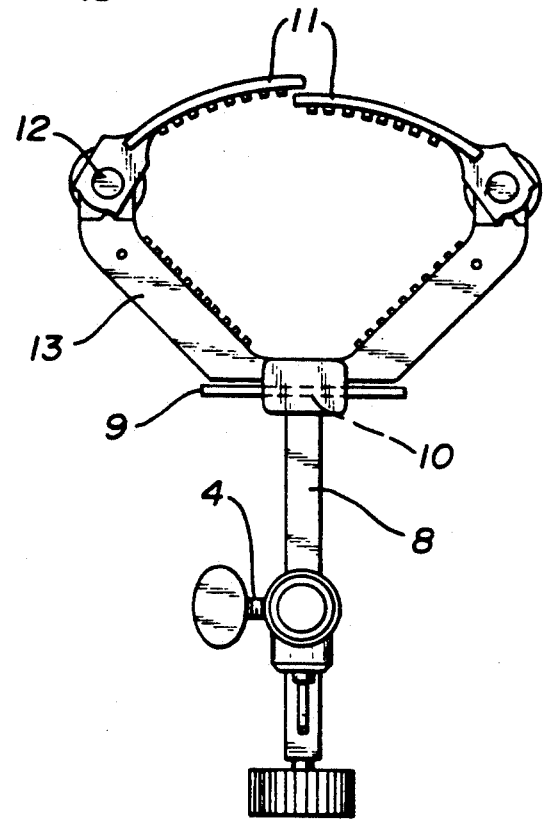
FIG. 4. is a top plan view of the ankle clamp and extension rail of the alignment instrument of FIG. 1.

As shown in FIG. 3, the cutting platform 6 has an improved slim configuration and an inner curved profile 15 adapted to fit against the tibia. It also has a central hole 16 adapted to accept the peg 17 of a stylus holder (FIG. 5) and holes 18 to accept location pins.

The distal portion of the instrument illustrated in FIG. 1 also carries a solid site guide 19 having a 5° site for correctly aligning the instrument relative to the tibia of a patient.

Figure 5:
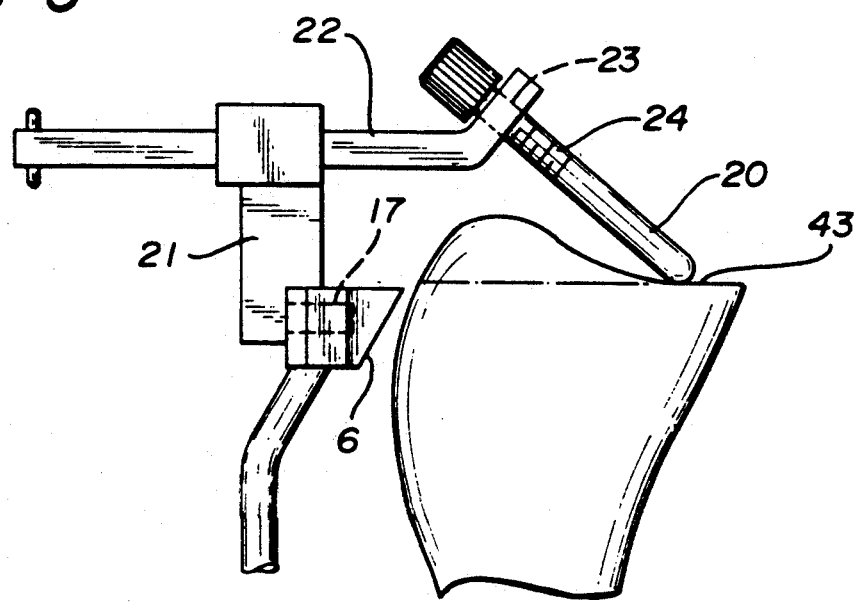
FIG. 5 is a side elevation of an adjustable stylus according to the invention.

FIG. 5 illustrates an adjustable stylus 20 for use in combination with the cutting platform 6 of the instrument illustrated in FIGS. 1-3, which comprises a solid base portion 21 having an extending peg adapted to be located in a cooperating hole in said cutting platform 6 to mount said base portion upon said cutting platform, an arm 22 extending upwardly and at an angle from said base, said arm having a distal end with a female screw thread 23 therein, and a stylus arm 20 having a distal end and a proximal end with a male screw thread 24, said male screw thread of the stylus arm being mated with the female screw thread of the upwardly extending arm, so that when the distal end of the stylus arm touches the tibial plateau 43 the cutting platform may be locked in its correct alignment for resection of the plateau and the stylus arm may then be withdrawn by unscrewing at its proximal end without disturbing the alignment of the cutting platform.

Figure 8:
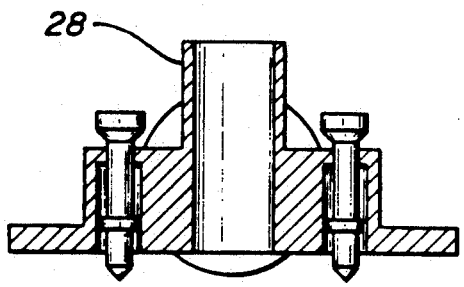
FIG. 8 is an end elevation of the template of FIG. 6.

FIGS. 6 to 8 illustrate a modular stem/fin template 25 for determining the peripheral size of a resected proximal tibia comprising a handle 26 carrying the template. The template, which may come in different sizes according to size of the tibia has a cut out portion 27 to accommodate the cruciate ligaments, and comprises a solid flat plate 25 defining the periphery of the resected proximal tibia, a raised cylindrical hollow tube 28 comprising a circular hole 29 to accept a stem punch (FIG. 9) and slots 30 radiating from said hole to accept a fin punch for aligning a stem/fin punch and also including an enlarged circular hole 31 for a drill around the end of each fin slot distal from said stem hole.

Figure 9:
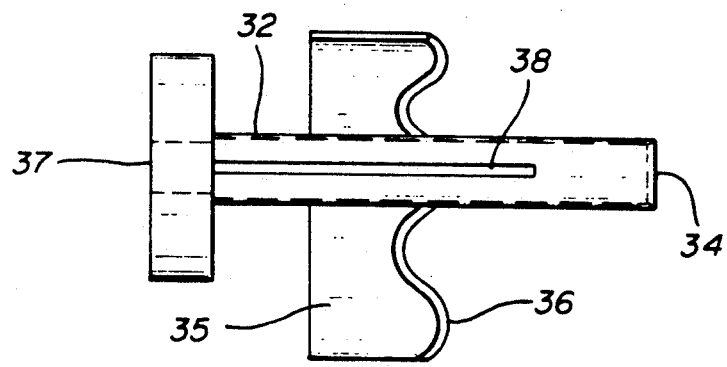
FIG. 9 is a side of elevation of a stem/fin punch.
Figure 10:
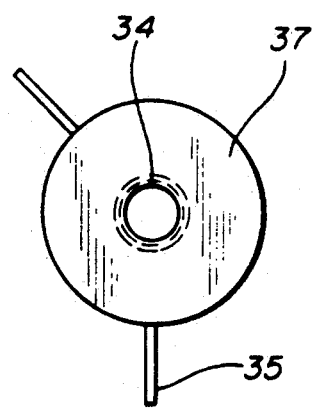
FIG. 10 is a plan view of the stem/fin punch of FIG. 9.

FIGS. 9 and 10 illustrate a stem/fin punch 32 comprising a central hollow cylindrical tube 33 with a distal chisel edge 34 and two fins 35 extending radially from said tube at a predetermined angle and each having a distal chisel edge. The proximal end of the punch terminates in a circular plate 37 adapted to be struck by a surgeon's mallet for punching out the bone to receive the stem and fins of a tibial implant.

The side of the cylindrical tube has a slot 38 into which a projecting peg 39 (FIG. 7) in the raised cylindrical hollow tube of the template may key thereby ensuring proper alignment of the punch within the template.

Figure 11:
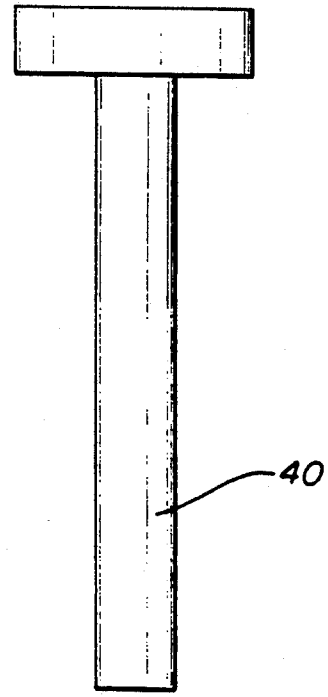
FIG. 11 is a side elevation of a push rod.

FIG. 11 illustrates a solid push rod 40 which fits into the hollow cylindrical tube of the stem/fin punch.

Figure 15:
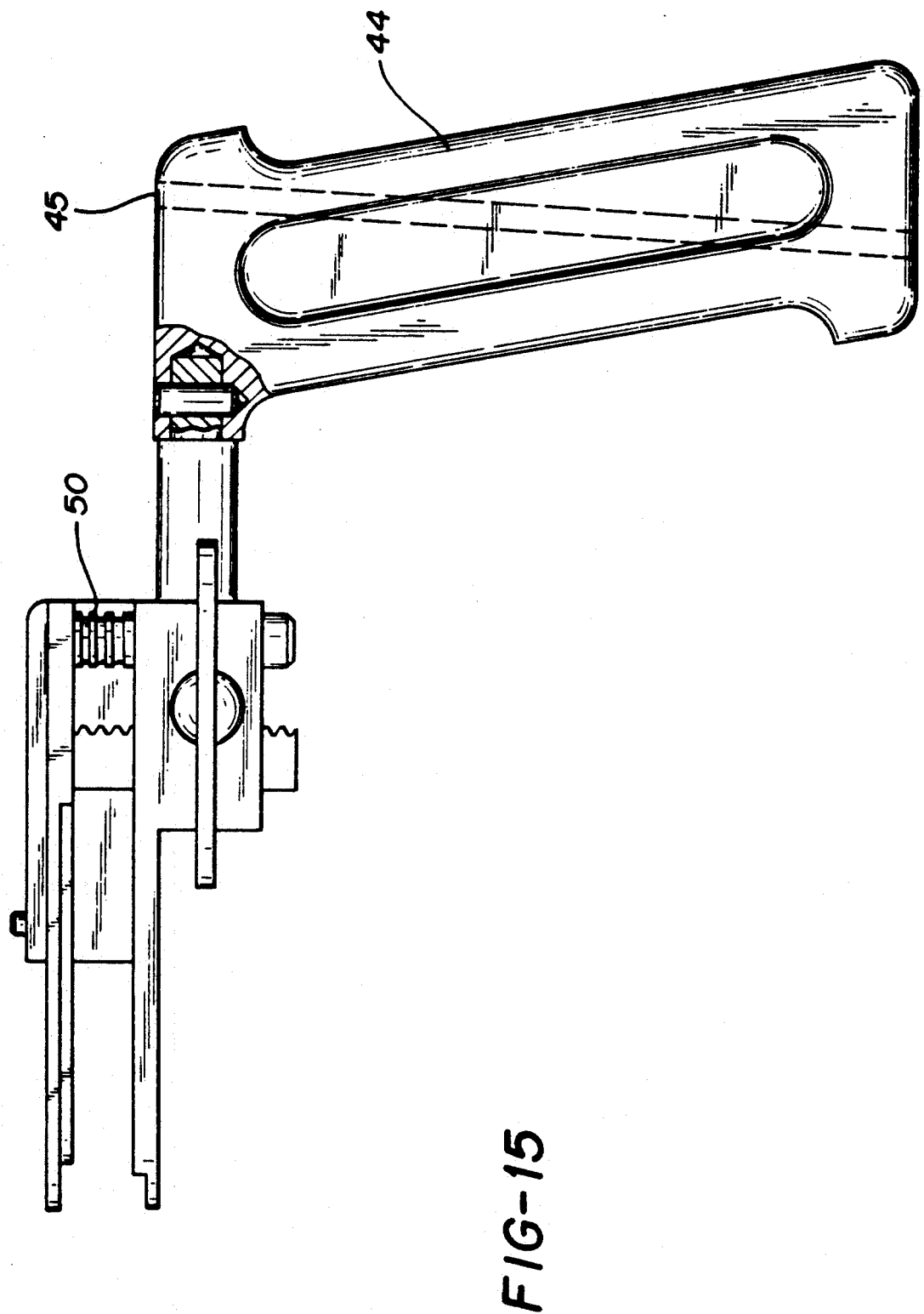
FIG. 15 is a side elevation of a femoral distractor.
Figure 16:
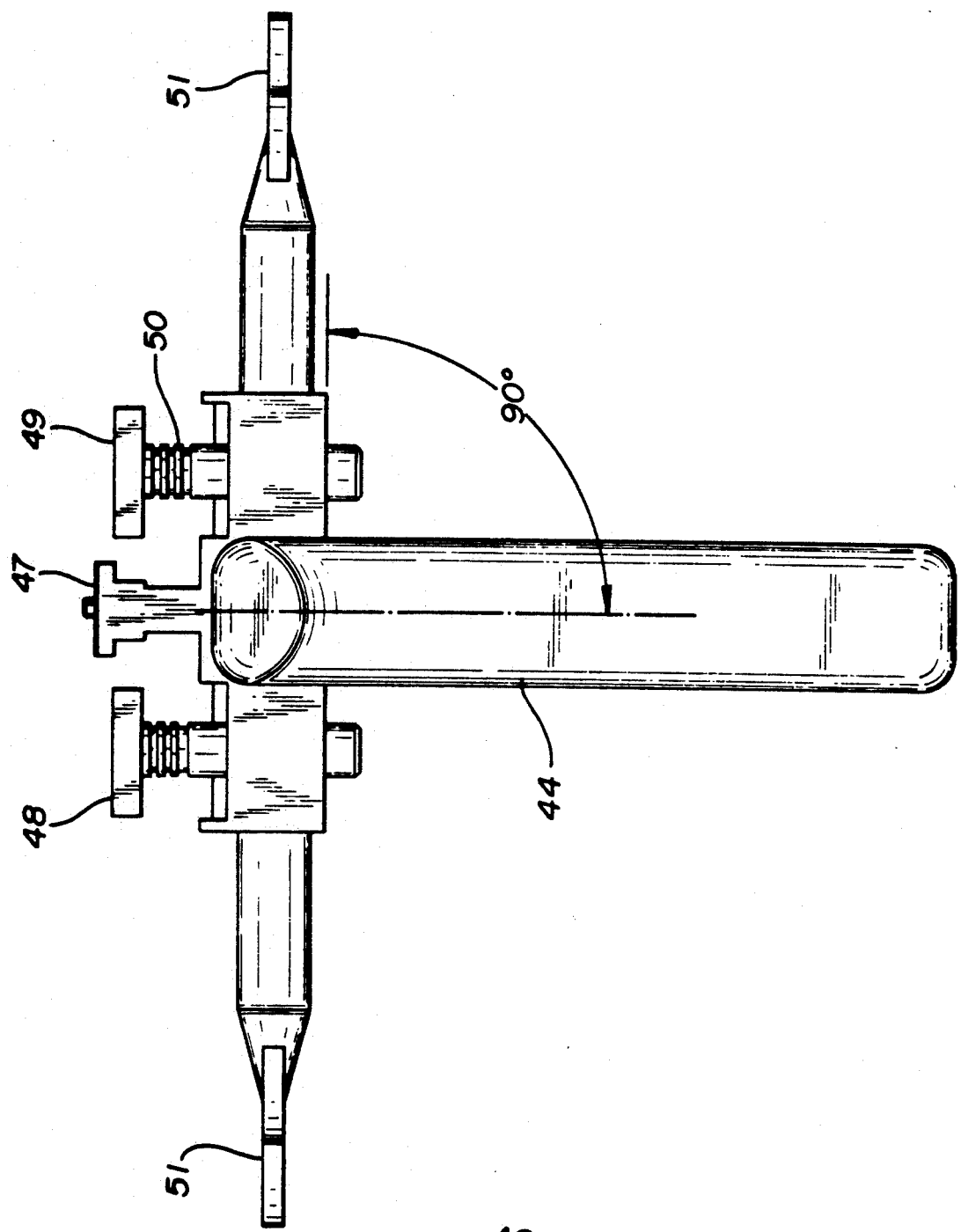
FIG. 16 is an end elevation of the distractor of FIG. 15.
Figure 17:
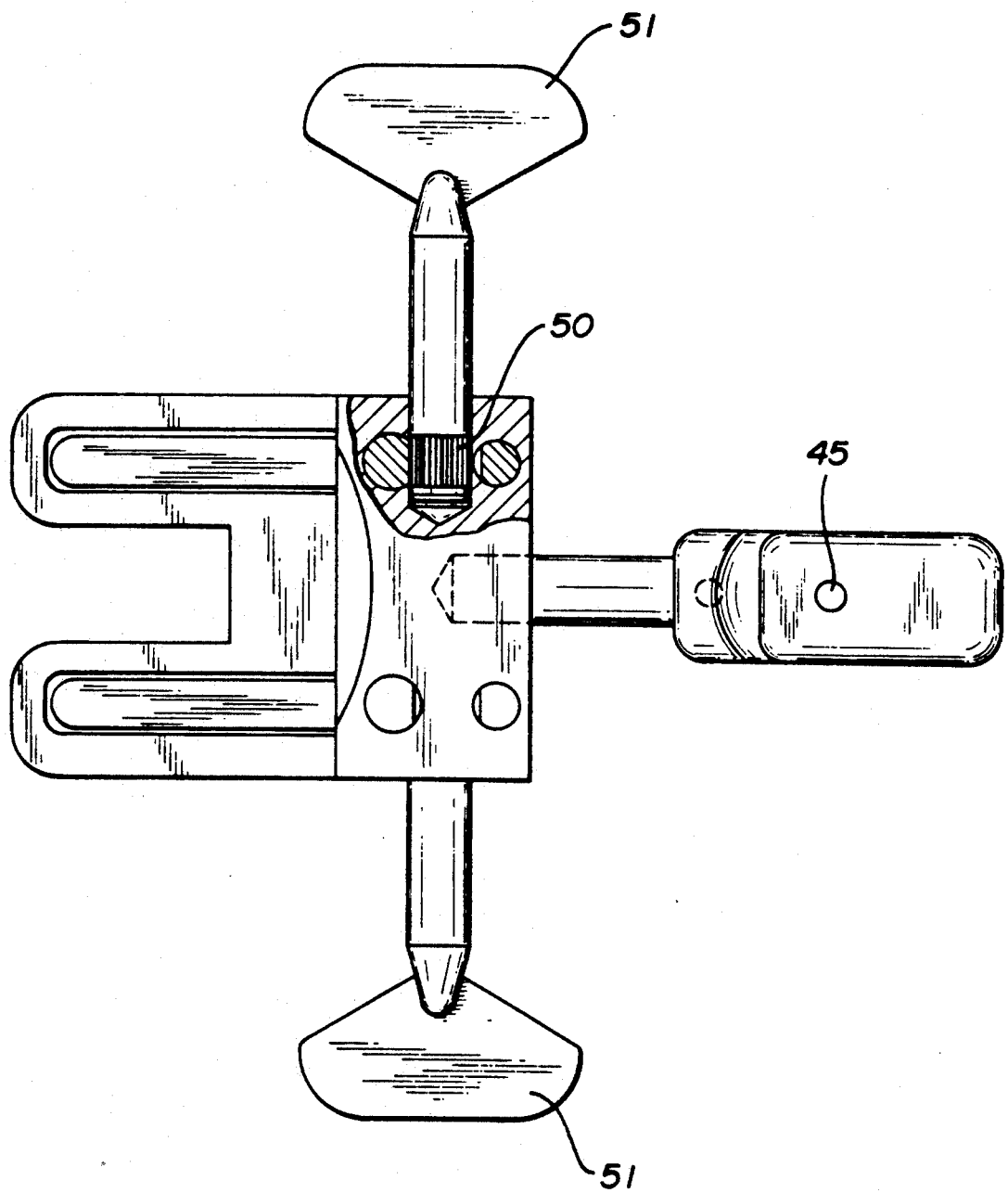
FIG. 17 is a bottom plan view of the distractor of FIG. 15.

FIGS. 12 to 14 illustrate an alignment fork 41 attached to an intramedullary rod 42 adapted to be introduced into a medullary canal of the patient;

FIGS. 15 to 17 illustrate a femoral distractor comprising a handle 44 having a vertical hole 45 there through for accommodating an alignment rod (not shown), a body 46, a rail 47 having a keyway 47' adapted to slide onto alignment fork 41 attached to medullary rod 42, a lateral arm 48 and a medial arm 49. Each arm may be separately raised or lowered by a rack and pinion mechanism 50, operated by a turn key 51.

Figure 18:
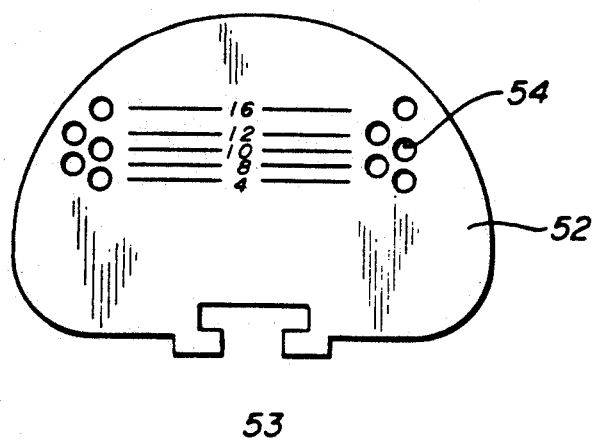
FIG. 18 is an end elevation of a modular drill guide.
Figure 19:
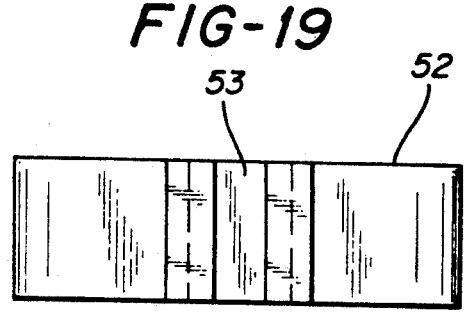
FIG. 19 is a bottom plan view of the drill guide of FIG. 18.

FIGS. 18 and 19 illustrate a drill guide 52 having a bottom groove 53 adapted to slide along a key element 53' of rail 47 of the femoral distractor and having a plurality of holes 54 for accepting locating pins (not shown).

Figure 20:
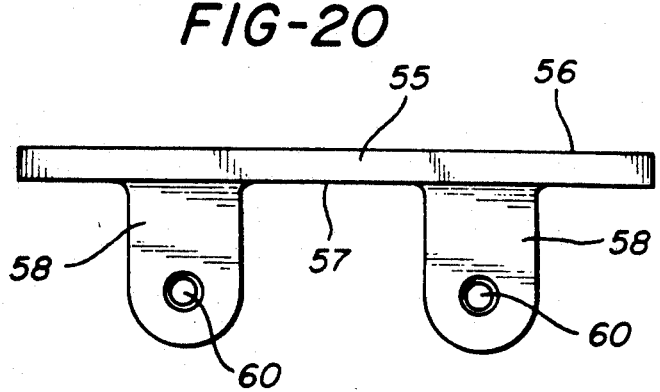
FIG. 20 is a side elevation of a distal cutting guide or distal femoral resection guide.
Figure 21:
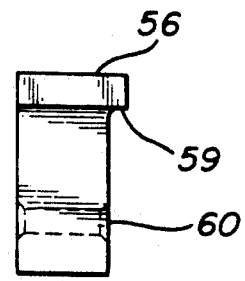
FIG. 21 is an end elevation of the guide of FIG. 20.
Figure 22:
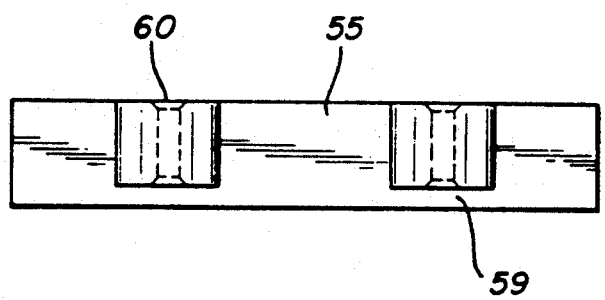
FIG. 22 is a bottom plan view of the guide of FIG. 20.

FIGS. 20 to 22 illustrate a distal cutting guide comprising a flat plate 55 having a top cutting surface 56 and a bottom surface 57 and integral flanges 58 extending from said bottom surface and each being inset 59 from one edge thereof, each of said flanges having a locating hole 60 extending therethrough.

Figure 23:
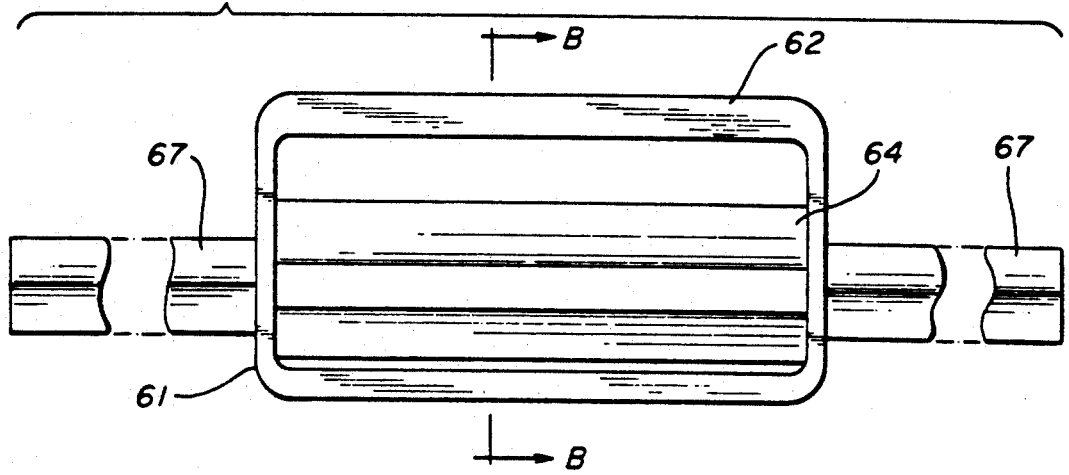
FIG. 23 is a side elevation of a modular cutting guide incorporating an anterior/posterior and chamfer resection guide.
Figure 24:
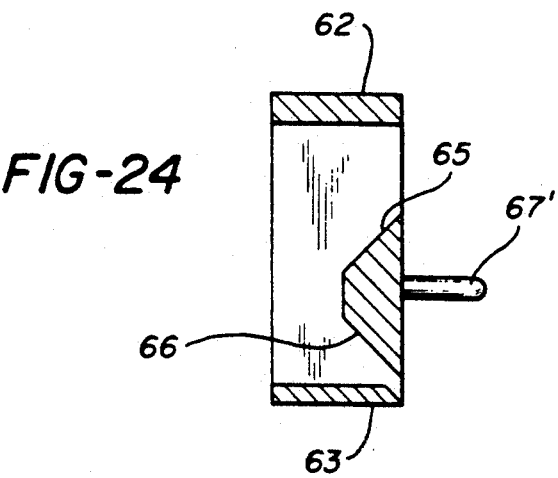
FIG. 24 is a cross-section through B—B of FIG. 23.

FIGS. 23 and 24 illustrate a modular cutting guide for guiding a saw blade to make cuts required for a femoral component of a total knee prosthesis, comprising a substantially rectangular block 61 having a flat top cutting surface 62 and a flat bottom cutting surface 63 and, located between said top surface and said bottom surface, an intermediate solid block 64 having an angled top surface 65 and an angled bottom surface 66, each of said angled surfaces providing a guide for making a chamfer cut. The intermediate solid cutting block carries pegs 67' for locating the guide in predrilled holes on the femur. The guide is held by handles 67 projecting from the sides of the block.

Figure 25:
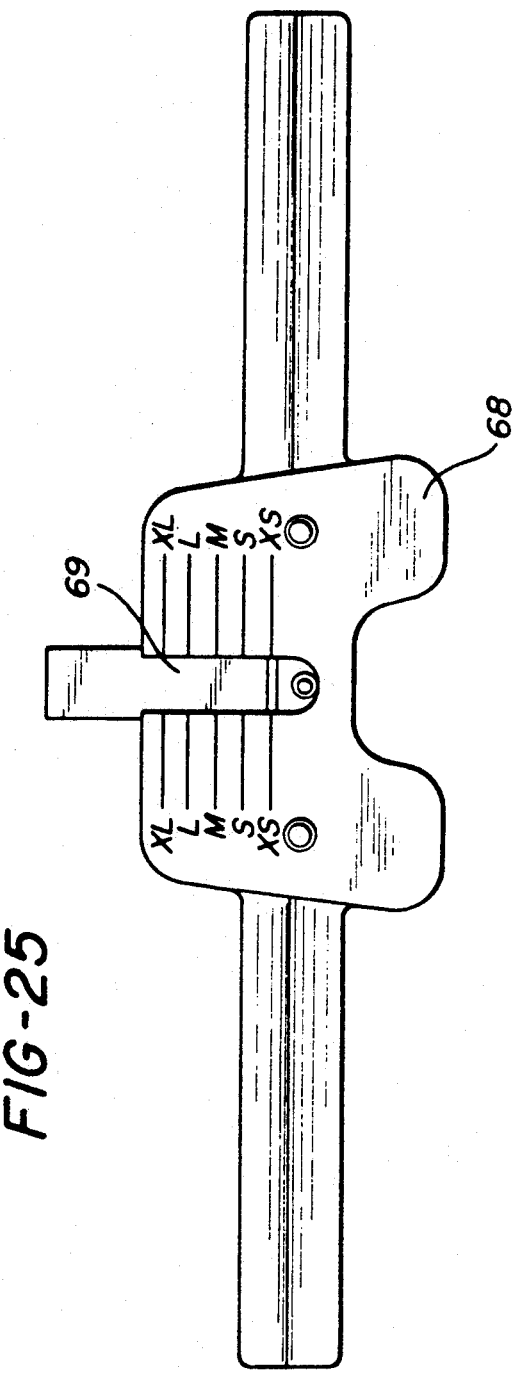
FIG. 25 is an end elevation of a femoral sizer.
Figure 26:
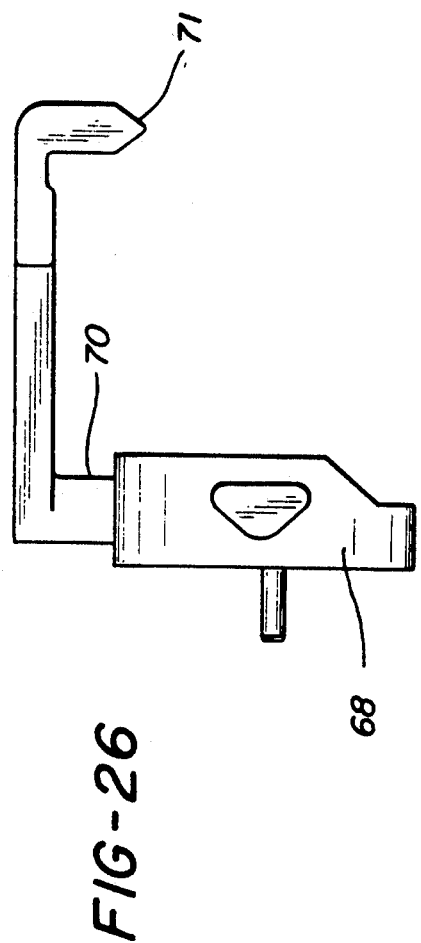
FIG. 26 is a side elevation of the sizer of FIG. 25.

FIGS. 25 and 26 illustrate a femoral sizer for determining the size of a patient's femur to prepare it for resection to receive a modular femoral prosthesis comprising a body portion 68 having locating holes, a central tubular orifice 69 for accepting a feeler element 70 and indicating means for indicating the depth of the feeler element within said orifice when the sizer 71 is located on the patient's femur, thereby providing a determination of the size required for a modular cutting guide.

FIGS. 27 and 28 illustrate a reamer guide for correct location of a reamer (FIG. 29) for preparing a cavity to locate a femoral prosthesis peg, which reamer guide comprises a flat plate 72 having a top surface 73 and a bottom surface 74, a hole 75 extending through the plate, a tubular bushing 76 extending from said top surface and lined up with said hole and locating pegs 77 extending from said bottom surface.

FIG. 29 illustrates a reamer having cutting edges 78 for reaming a cavity to accept the stem of a femoral component prosthesis.

Figure 30:
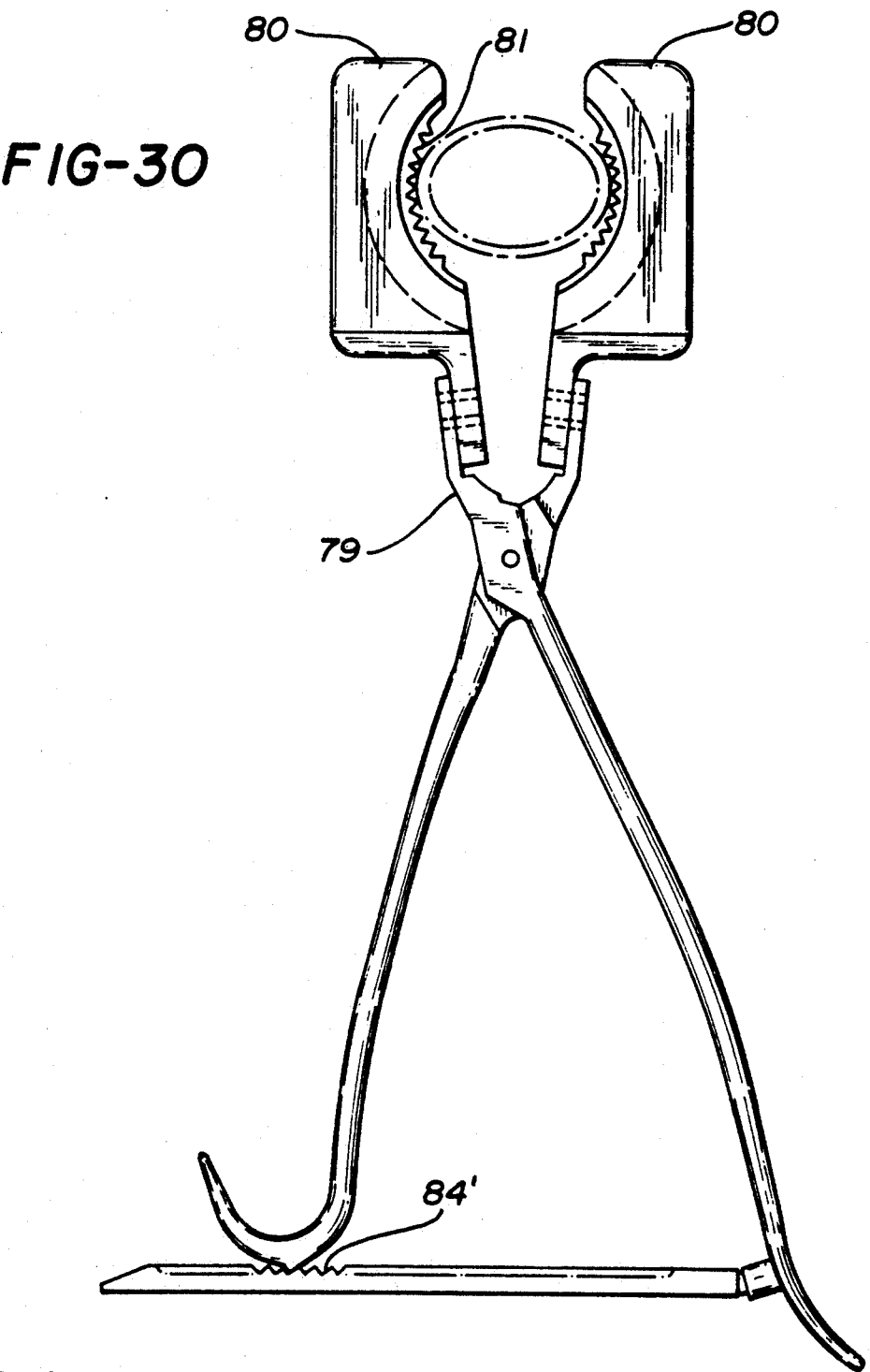
FIG. 30 is a plan view of a patella resection guide and clamp.
Figure 31:
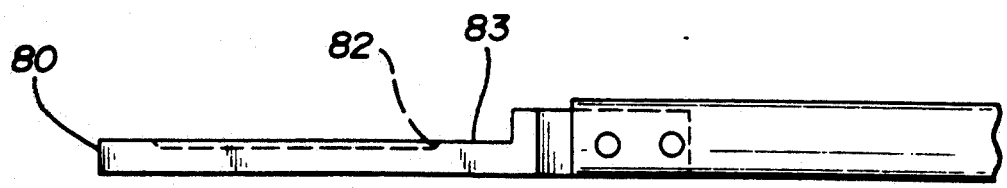
FIG. 31 is a partial side elevation of one of the jaws of the patella resection guide of FIG. 30.
Figure 32:
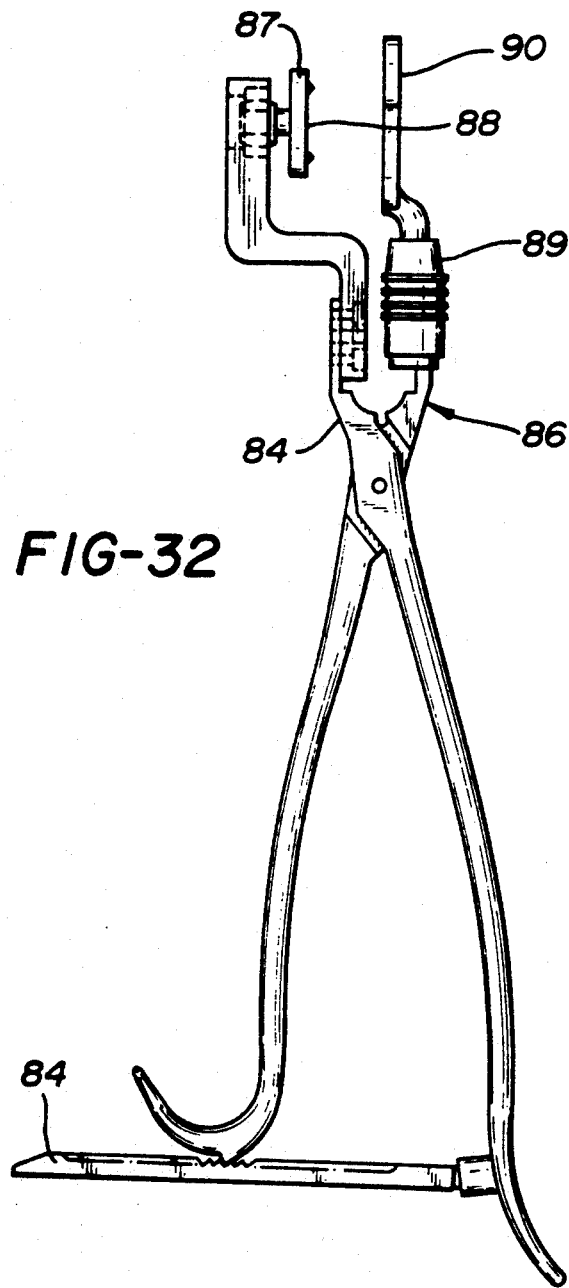
FIG. 32 is a side elevation of a patella handling instrument holding a patella template.

FIGS. 30 and 31 illustrate a patella resection guide comprising a scissor-type clamp 79 having distal gripping arms 80, each of said arms defining a cutting surface and gripping teeth 81, said gripping teeth being inset 82 below the plane 83 of the associated cutting surface.

The proximal end of the device has a ratchet arm 84 to prevent the clamp from slipping.

FIGS. 32, 33, 35, 36 and 37 illustrate a patella handling instrument having an interchangeable modular template and clamp, comprising a scissor-type member 84 having a first pivotal arm 85 with a distal end and a second pivotal arm 86 with a distal end, said first arm having a swivable platform 87 located at its distal end, the surface 88 of said platform facing inwardly toward said second arm and said second arm having means 89 to interchangeably grip and hold either: (i) a modular patella template 90 having holes to accept drills, or (ii) a clamp member 91 adapted to clamp a patella prosthesis to a resected patella.

Figure 35:
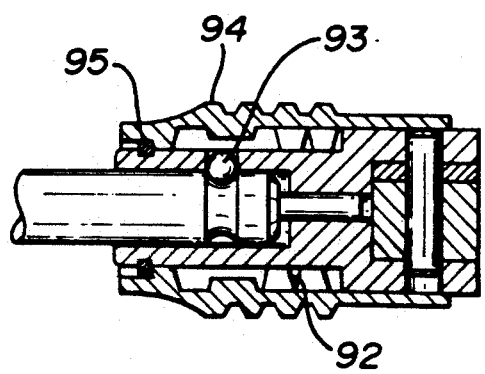
FIG. 35 is an enlarged sectional view of a quick-connect device for interchanging and retaining elements of the instrument of FIG. 32.

The preferred means for interchanging the template and the clamp member is a quick-connect device illustrated in detail in FIG. 35.

The quick connect device comprises a compression spring 92, a ball 93, a coupling 94 and a retaining ring 95.

Figure 33:
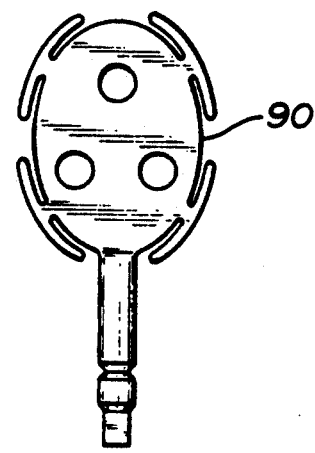
FIG. 33 is a plan view of a modular patella template for use with the instrument of FIG. 32.
Figure 34:
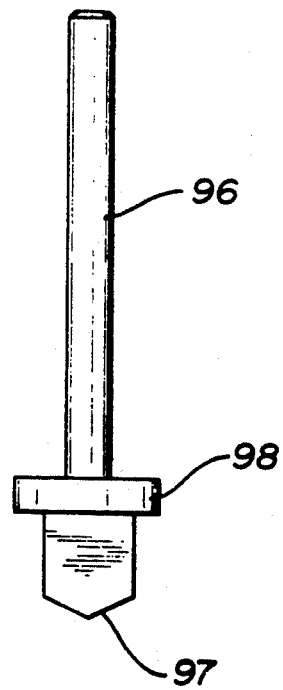
FIG. 34 is a side elevation of patella drill with stop for use with the template of FIG. 33.

FIG. 34 illustrates a drill bit 96 with a chisel edge 97 and a stop 98 for drill holes in a patella using the template illustrated in FIG. 33.

Figure 38:
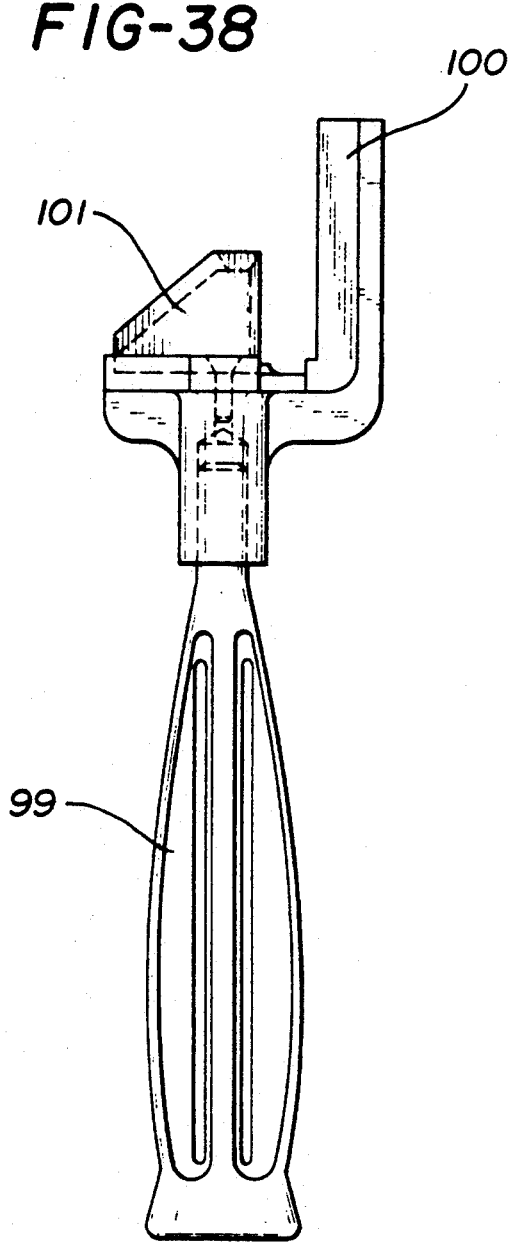
FIG. 38 is a side elevation of a femoral stabilizer box chisel.
Figure 39:
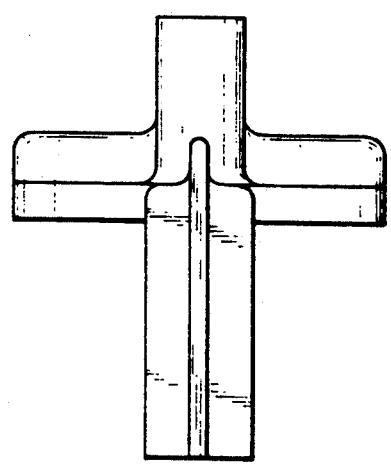
FIG. 39 is a top plan view of the chisel of FIG. 38.
Figure 40:
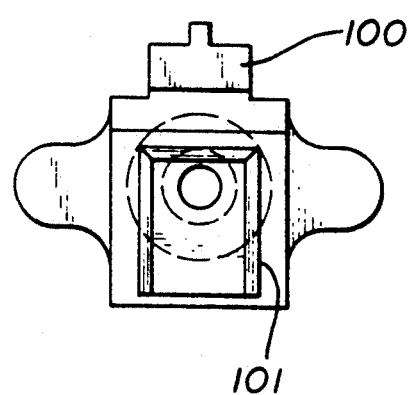
FIG. 40 is an end elevation of the chisel of FIG. 38.

FIGS. 38 to 40 illustrate a femoral stabilizer box chisel for excavating a bone to accept a posterior stabilized femoral component which comprises a handle 99, a locator housing 100 extending from said handle and a box chisel 101 extending parallel to said locator housing and having a cutting profile for cutting the required cavity to accept the peg of the stabilized component.

Figure 41:
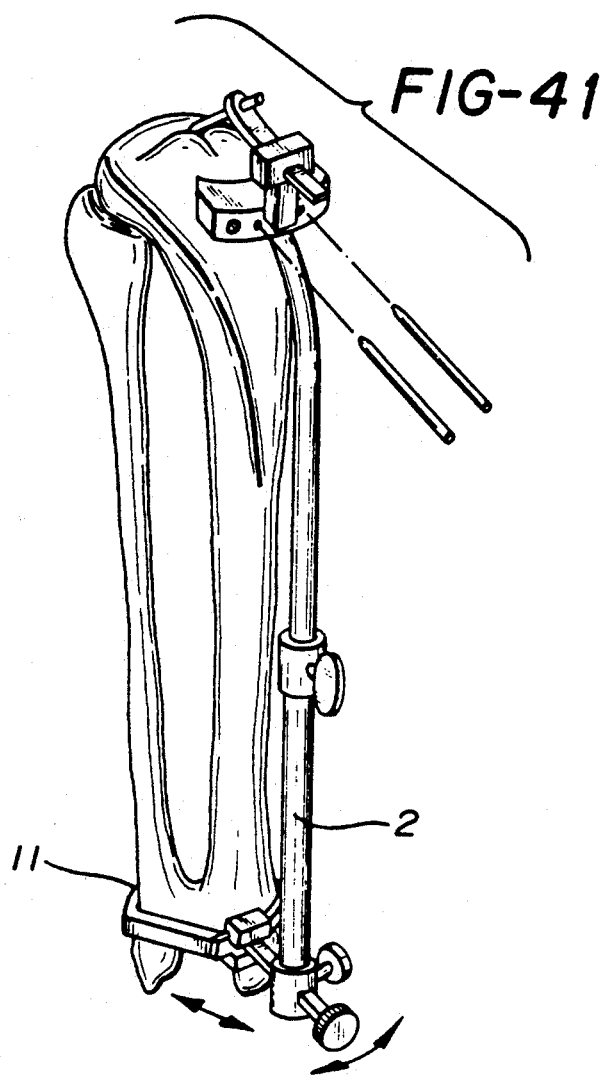
Figure 42:
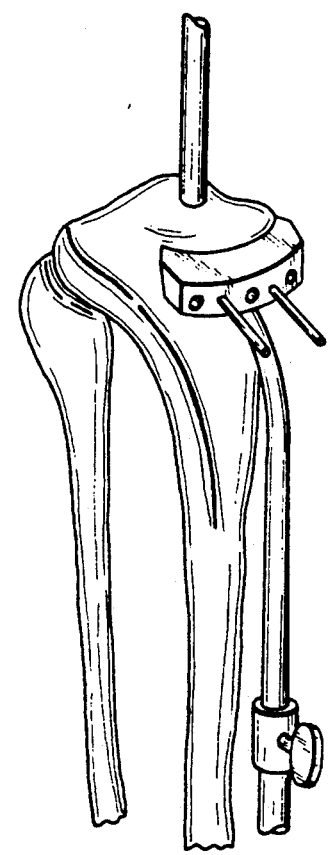
Figure 43:
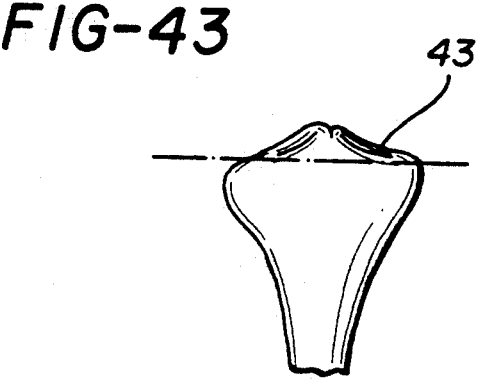

The surgical procedure for utilizing the instrumentation of the present invention will now be described with reference to the schematic drawings of FIGS. 41 to 43.

(1) Cutting the Proximel Tibia

The patient's knee is flexed past 90° and the tibia is drawn forward. As shown in FIG. 41 the lower clamp arms 11 of the upper tibial cutting guide 6 are opened and clamped around the ankle joint proximal to the medial malleolas. The distal end has two adjustments, one each for anterior/posterior (A/P) and medial/lateral (M/L).

The alignment tube 2 may be shifted about 2.5 mm. to compensate for the presence of the fibula. The tube is slid along the A/P rail 8 to a specified mark to establish a 3°–5° posterior slope. The site guide 19 on the anterior surface of the tube serves as a visual aid. The level of the cutting platform is positioned relative to the lowest point on the tibial plateau using the tibial stylus as a guide. Two ⅛" pins are used to fix the cutting platform to the proximal tibia so that accurate bone cuts can be made.

The curvature R in the rod which connects the cutting platform to the alignment tube mimics the posterior angulation of the proximal tibia. This positions the cutting platform close to the tibial plateau and will allow a standard sized saw blade to cut the entire surface of the proximal tibia. The cutting platform is contoured to match the curvature of the anterior tibial plateau.

Preparing a Site for the Prosthesis

The peripheral size of the resected proximal tibia is determined using the stem/fin punch templates (FIGS. 44 and 45). The size which best covers the peripheral cortical rim is chosen. Using the alignment rod through the hold in the handle, rotational alignment of the template is established by lining up the alignment rod and tibial shaft in the frontal plane. The two captured pins are tapped into the proximal tibia to secure the template. The appropriate sized stem/fin punch is chosen and introduced into the cylindrical projection on the template. Rotational orientation of the punch is established by engaging the wings within the slots in the cylinder. Using a mallet the punch is driven into the tibia until the driving platform bottoms on the top of the cylinder. Because the stem portion of the punch is hollow, but bone will fill this space. Choose the appropriate size plug pusher 40 and drive it into the bone of the punch stem (FIGS. 11 and 45). This will force the bone which occupies the space distally, compacting it. This bone will serve as a cement restrictor in the event that bone cement is utilized in the fixation of the tibial baseplate. When bone cement is used, two holes 31 are drilled in the medial and lateral plateaus, using the holes 31 in the template as a guide for the drill bits 102 which have been marked with an appropriate depth stop (FIG. 44).

Femoral Preparation

Figure 46:
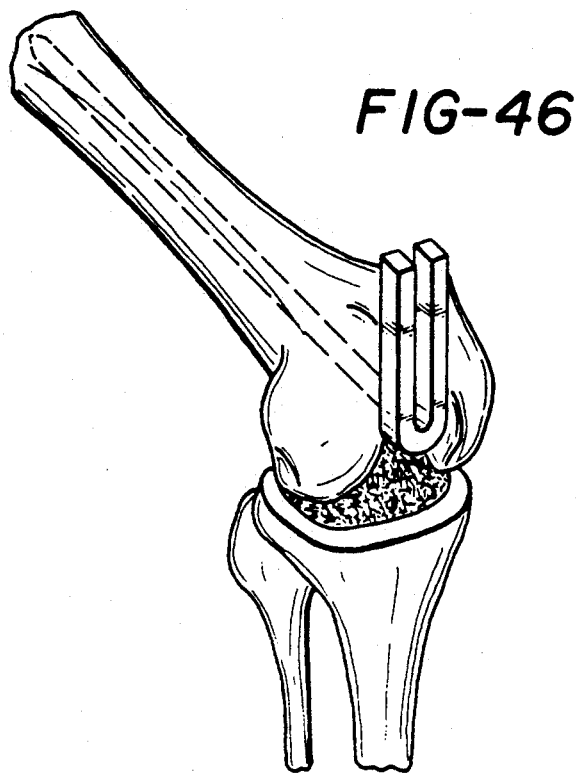

The lateral anterior prominence is resected from the distal femur for better seating of the diatal femoral cutting block to be used later. A 5/16" (8 mm) starter hole is drilled in line with the medullary canal. The location of the drill hole should be midway between the medial and lateral femoral condyles just anterior to the origin of the posterior cruciate. The direction of the drill bit should be in line with the longitudinally axis of the femur in both planes. The right or left alignment fork is introduced into the medullary canal (FIG. 46).

Figure 47:
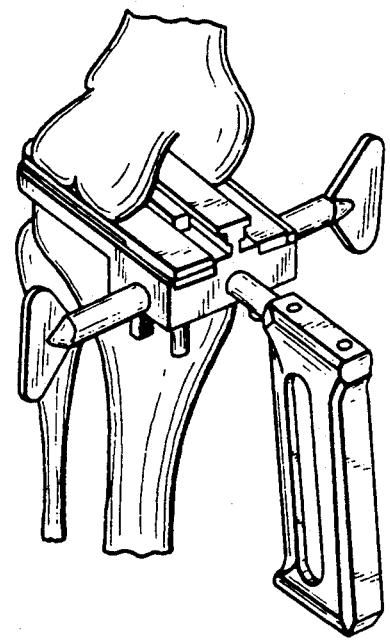

The femoral distractor is slid onto the alignment fork and the leg extended (FIG. 47). The distractor is now keyed to the femur at the appropriate angle of valgus from the mechanical axis in the frontal plane and perpendicular in the sagittal plane.

Care is taken that the femoral distractor is sitting flush on the cut proximal tibia. Distract the lateral and medial arms of the distractor up to the femoral condyles with the knee in full extension. If the lateral and medial ligaments are imbalanced, carry out appropriate soft tissue releases at this time. Overall leg alignment can be further checked with the long alignment rod through the handle of the distractor. The alignment rod should bisect the malleoli distally and be one inch medial to the anterior-superior spine proximally. Read off the tibial thickness markings as seen in FIG. 45, and select the lower value between lateral and medial.

Figure 48:
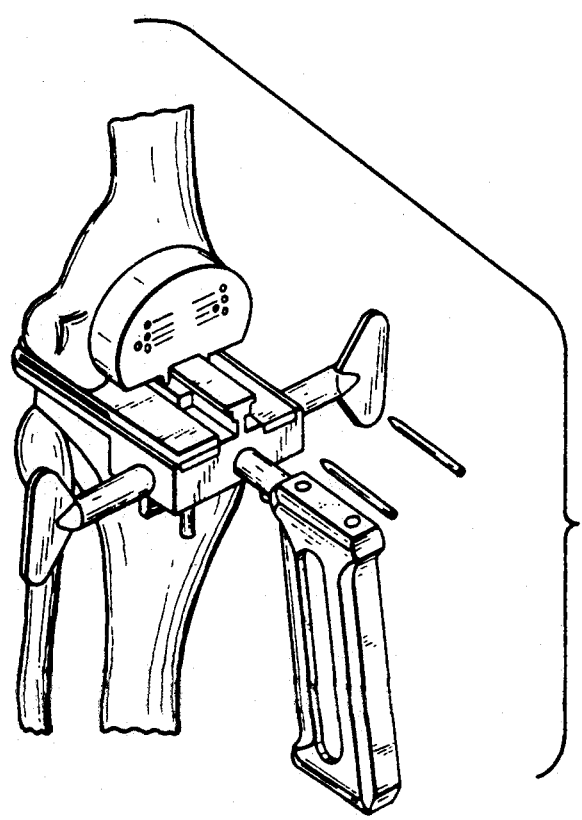

Slide the drill guide up to the anterior femur and tap two 3 mm pins through the holes corresponding to the just selected tibial thickness (FIG. 48).

Slide the drill guide off, leaving the pins in place. Release the tension on the distractor and remove. Flex the knee to 90° and remove the alignment fork. Slide the distal cutting guide onto the pins. The block is stepped to allow the cutting surface to sit close to the surface to be cut. Using an oscillating saw, resect the distal femoral condyles. The cut should be perpendicular to the long axis of the femur in the sagittal plane, and in the appropriate degree of valgus (FIG. 49).

Maintain the leg in 90° of flexion and insert the distractor so that it rests flat on the cut proximal tibia. Distract to the same amount as in extension, or slightly less if a more lax posterior cruciate ligament is preferred. Slide the drill guide flush with the cut distal surface and tap two 3 mm pins thru the previously selected holed (FIG. 50). Slide the drill guide off, release tension, and remove the distractor.

Slide the body of the A-P sizer onto the pins (FIG. 51) and engage the feeler into the hole in the body. Lower and rotate the feeler until it touches the high point of the anterior cortex. Read the appropriate femoral size by sighting the level of the hash mark. Remove the instrument and pins.

Select the appropriate size A-P/chamfer combo block (FIG. 52), and engage the fixed pins in the undersized holes in the distal femur. Tap the block until it sits flush against the distal femur. With this block in place, all femoral cuts can be made. The A-P cuts are made using the top and bottom surfaces of the outer box. The chamfer block is inset allowing visibility of the bone surfaces to be cut.

The hole for the central stem is prepared once the trial is in place by inserting the peg reamer through the central hole on the femoral trial and reaming to the appropriate depth which is determined by a marking on the reamer.

If a stabilizer femoral component is used, the bone must be excavated to prepare a site for the stabilizer box. Choose the appropriate size stabilizer chisel (FIG. 40). Rest the anterior skid on the cut anterior femur and position the chisel midway between the femoral condyles. With a mallet blow, impact the chisel to its full depth to remove the appropriate amount of bone.

Patella Preparation

The patella resection guide is used to grip the patella and serves as a guide for the oscillating saw. The jaws of the resection guide clamp the medial/lateral edges of the patella at the level of the proximal quadriceps and distal patellar tendon insertions. The top of the jaws are broad and flat and will guide the oscillating saw, making a flat cut.

The size of the patella surface is assessed using the patella template 90 which includes 3 sizes in one. Once the appropriate size is determined, holes to accept the three lugs are drilled into the patella surface by inserting the patella drill through the holes on the patella template, and drilling to an appropriate depth.

At this point, all bone surfaces have been prepared to accept the prosthetic components. Each prosthesis is inserted with its dedicated insertional tool.

The femoral inserter keys into the slots on the outside edges of the femoral condyles. Varying femoral sizes are accomodated by a gearing mechanism within the inserter. A push pad is forced against the intercondylar region, and locks the prosthesis to the inserter. It can now be impacted onto the bone.

The tibial inserter keys and locks into under cuts provided on the tibial baseplate, a sliding mechanism is used to accommodate varying prosthetic sizes.

The patella forceps clamp (FIG. 36) is used to press the patella button into position, and maintain this position while the bone cement is setting.

Implant Components

An important feature of the implant system is its modularity and the fact that it has been designed for both cemented use and cementless press-fit applications utilizing the same prosthetic components.

All bone contact surfaces of both the femoral components and tibial baseplates are generally broad and flat and contain no depressions, historically used as a reservoir for excess bone cement. Rather, these bone contact surfaces are roughened by a blasting operation which is ideal, both for adhering to bone cement and for bone ingrowth in the absence of cement.

On the femoral component, fixation pegs have been removed from the condyles where they are most often found and have been replaced by one central stem. This allows for minimal disturbance of the distal condyles to enhance loud transmission in a press-fit mode.

The tibial baseplates have a unique stem/fin configuration. The wings extend outwardly and angle posteriorly. This positions the tabs in the area of the strongest cancellous bone on the proximal tibial plateau, providing restraint against rotational forces. The wings sweep upward as they near the central stem allowing for a uniform, uninterrupted cement mantle in a cemented mode.

The patella prosthesis is suitable for cemented fixation only.

The modularity of the system is a result of extensive interchangeability of the different components. This modularity allows for precise fitting of individual patient anatomy and accommodates varying degrees of necessary prosthetic stability. The tibial baseplates have been designed with undercuts, which allow both styles (PC/TC and stabilizer) of inserts to be assembled to them at the time of surgery.

Each insert is designed to accept three sizes of corresponding femoral components and are offered in varying thicknesses. The PC/TC inserts can be used when the posterior cruciate ligament is either present or absent.

The patella flanges of both the primary and stabilizer femoral components are designed to accept any size patella prosthesis.

The prosthetic system is also applicable when the patient has bone stock deficiencies. Metallic bone wedges for both the tibial baseplate and femoral components are provided. They are directly attached to the implant components via bone cement to fill voids in the host bone cite.

The wedges have the same roughened texture as the tibial and femoral components, this surface is ideal for cement adhesion at both the wedge/prosthesis and wedge/bone interface.

The wedges are offered in sizes which correspond to the tibial and femoral component sizes.

The Posterior Cruciate Total Condylar Knee System consists of femoral, patellar and tibial components in varying sizes to accommodate differences in patient anatomy.

Femoral Component

This component made from cast Vitallium ® alloy is symmetrical about the vertical axis so as to be suited for replacement of the bearing surface of either the left or right femur and is designed with a neutral patellar groove. The internal surfaces of the component are flat, containing no depressions and are roughened (by grit blasting) to allow cement bonding. A central tapered stem is located at the base of the anterior chamfer and extends vertically, perpendicular to the distal surface.

The articulating surfaces of the device—two femoral condyles and a patellar flange—are highly polished. The broad femoral condyles present a large medial-lateral radius to evenly distribute stresses to the tibial component. The patellar flange is deep and is designed to mate with the patellar prosthesis or the natural bone.

Each femoral component size is designed to mate with either its similar size tibial insert or one size larger or smaller.

Tibial Component

The tibial prosthesis is a two piece design consisting of a cast Vitallium ® tray and UHMW Polyethylene inserts which are assembled to the tray at the time of surgery. The baseplates are offered in varying sizes to optimally fit the peripheral shape of the tibial plateau. The UHMW Polyethylene inserts mate with the corresponding size tibial baseplate and are offered in varying thicknesses to compensate for degrees of ligament laxity.

The tibial baseplate consists of a central stem (available in varying lengths) with supporting ribs which flare outwardly and posteriorly in the medial and lateral direction. The undersurface of the tray and stem are grit blasted, to provide a roughened surface for cement adhesion.

The articulating surface geometry of the tibial inserts are designed to provide anatomic rollback, flexion-extension and axial rotation. The anterior portion of the insert is raised superiorly to provide resistance to subluxation should the posterior cruciate ligament be resected. Provision is made to allow clearance for the posterior cruciate ligament should it remain intact.

The interlocking mechanism of the tibial component operates by means of a snap fit between the metal baseplate and the UHMW Polyethylene insert. The metal baseplate is designed with two undercuts at the posterior margins on either side of the posterior cruciate ligament cutout. The anterior portion is equipped with a raised element which contains an undercut rim. The plastic insert has two elongated tabs which, when slid into position from anterior to posterior, engage the posterior undercuts on the metal baseplate. When fully engaged a downward force is applied to the anterior portion of the plastic insert which causes a relieved plastic tab to flex back and under the anterior undercut rim on the baseplate. (An audible "Snap" may be heard as the components are fully engaged). This action mechanically secures the plastic insert within the confines of the metal baseplate.

Patellar Component

The patellar component is manufactured from UHMW Polyethylene and is offered in varying sizes to fit the peripheral shape of the resected patella.

The bearing surface geometry is asymmetric about the proximal/distal axis to provide a left or right orientation. This asymmetry allows for anatomic tracking against the highly polished surface of the femoral components's patellar flange.

The undersurface consists of three lugs and a central depression which provides interlock for bone cement to securely fix the prosthesis to the resected patella.

The Stabilizer Total Knee System consists of femoral, tibial and patellar components in varying sizes to accommodate differences in patient anatomy.

Femoral Component

This component made from cast Vitallium ® alloy is symmetrical about the vertical axis so as to be suited for replacement of the bearing surface of either the left or right femur and is designed with a neutral patellar groove. The internal surfaces of the component contain no depressions and are roughened (by grit blasting) to enhance cement bonding.

The articulating surfaces of the device—two femoral condyles, intercondylar cavity, and a patellar flange—are highly polished. The broad femoral condyles present a large medial—lateral radius to evenly distribute stresses to the tibial component. The patellar flange is deep and is designed to mate with the patellar prosthesis or the natural bone. The intercondylar cavity is designed to mate with an element of the tibial insert described below.

Each component size is designed to mate with either its similar size tibial insert or one size larger or smaller.

Tibial Component

The tibial prosthesis is a two-piece design consisting of a cast Vitallium ® tray and UHMW Polyethylene inserts which are assembled to the tray at the time of surgery. The baseplates are offered in varying sizes to optimally fit the peripheral shape of the tibial plateau. The UHMW Polyethylene inserts mate with the corresponding size tibial baseplate and are offered in varying thicknesses to accommodate differences in patient anatomy.

The tibial baseplate consists of a central stem (available in varying lengths) with supporting ribs which flare outwardly and posteriorly in the medial and lateral direction. The undersurface of the tray and stem are grit blasted, to provide a roughened surface for cement adhesion.

The articulating surface of the tibial insert contains medial and lateral depressions which are designed to articulate with the condyles of the femoral component allowing anatomic flexion-extension and internal-external rotation. A post, extending proximally, is positioned between the medial and lateral articulating surfaces. The anterior face is angled posteriorly to avoid infringement of the patella.

The posterior surface is angled anteriorly to present a sloping surface on which the curved portion of the femoral intercondylar cavity may articulate against. When the knee flexes in the absence of the posterior cruciate ligament this articulation produces posterior rollback of the femur as in natural knee motion.

We claim:

1. A modular cutting guide for guiding a saw blade to make cuts required for a femoral component of a total knee prosthesis, comprising a substantially rectangular frame having a top wall and a bottom wall, each of said walls being defined by substantially parallel planar outer and inner surfaces wherein each outer surface provides a flat cutting plane and the inner surfaces define an open window within which is located an intermediate solid block having an angled top surface and an angled bottom surface, each of said angled surfaces providing a guide for making a chamfer cut, said angled bottom surface being spaced apart from the bottom inner surface of said block defining said window a first distance greater than the thickness of the saw blade and said angled top surface being spaced apart from the top inner surface of said block, defining said window, a distance greater than said first distance to provide a surgeon with a clear view of the surfaces being cut.

* * * * *